(12) United States Patent
Lai et al.

(10) Patent No.: US 9,563,262 B2
(45) Date of Patent: Feb. 7, 2017

(54) ELECTRONIC APPARATUS AND INFORMATION PROCESSING METHOD

(71) Applicant: Lenovo (Beijing) Co., Ltd., Beijing (CN)

(72) Inventors: Xuefeng Lai, Beijing (CN); Xi Wan, Beijing (CN); Xiaohua Jiang, Beijing (CN); Xiaodong Yu, Beijing (CN); Weicheng Li, Beijing (CN)

(73) Assignee: LENOVO (BEIJING) CO., LTD., Haidian District, Beijing (CN)

( * ) Notice: Subject to any disclaimer, the term of this patent is extended or adjusted under 35 U.S.C. 154(b) by 149 days.

(21) Appl. No.: 14/477,164

(22) Filed: Sep. 4, 2014

(65) Prior Publication Data

US 2015/0067366 A1    Mar. 5, 2015

(30) Foreign Application Priority Data

Sep. 5, 2013  (CN) .......................... 2013 1 0400189
Feb. 25, 2014  (CN) .......................... 2014 1 0065588

(51) Int. Cl.
| | |
|---|---|
| G06F 1/00 | (2006.01) |
| G06F 1/32 | (2006.01) |
| A61B 5/00 | (2006.01) |
| G06F 1/16 | (2006.01) |

(52) U.S. Cl.
CPC ............. *G06F 1/3293* (2013.01); *A61B 5/681* (2013.01); *G06F 1/163* (2013.01)

(58) Field of Classification Search
CPC ......... G06F 1/3293; G06F 1/163; A61B 5/681
USPC ...... 368/10, 70, 226, 64; 345/173, 157, 650, 345/90.3; 713/320, 323; 715/19; 725/61; 327/543

See application file for complete search history.

(56) References Cited

U.S. PATENT DOCUMENTS

| | | | |
|---|---|---|---|
| 6,809,724 B1 * | 10/2004 | Shiraishi ................. | G06F 1/163 345/157 |
| 7,251,197 B2 * | 7/2007 | Yoshida ................. | H04B 1/385 368/10 |
| 8,437,808 B2 | 5/2013 | Kashikar | |
| 8,515,505 B1 | 8/2013 | Pattikonda | |

(Continued)

FOREIGN PATENT DOCUMENTS

| | | |
|---|---|---|
| CN | 2332116 Y | 8/1999 |
| CN | 101433061 | 5/2009 |

(Continued)

OTHER PUBLICATIONS

Wikipedia. E-Paper, pp. 1-12.*

(Continued)

*Primary Examiner* — Aurel Prifti
(74) *Attorney, Agent, or Firm* — Brinks Gilson & Lione; G. Peter Nichols

(57) ABSTRACT

An electronic apparatus includes a first processing unit for executing an operation of a first type; a second processing unit for executing an operation of a second type, with the average power consumption of the second processing unit being less than average power consumption of the first processing unit; a sharing unit connected to the first processing unit and the second processing unit and for operating cooperatively with either or both of the first processing unit and the second processing unit selectively according to predetermined condition; and a fixing unit for fixing relative position relation of the electronic apparatus with the user.

19 Claims, 12 Drawing Sheets

(56) References Cited

U.S. PATENT DOCUMENTS

| | | | |
|---|---|---|---|
| 8,548,528 B2 | 10/2013 | Kim | |
| 8,571,605 B2 | 10/2013 | Park | |
| 9,288,836 B1* | 3/2016 | Clement | H04W 84/18 |
| 9,442,570 B2* | 9/2016 | Slonneger | G06F 3/017 |
| 2009/0259865 A1* | 10/2009 | Sheynblat | G06F 1/3203 |
| | | | 713/323 |
| 2010/0048253 A1 | 2/2010 | Park | |
| 2010/0112964 A1* | 5/2010 | Yi | G04G 21/04 |
| | | | 455/90.3 |
| 2010/0289740 A1* | 11/2010 | Kim | G04G 21/04 |
| | | | 345/157 |
| 2011/0124376 A1 | 5/2011 | Kim | |
| 2011/0255379 A1* | 10/2011 | Vidal | G04G 9/047 |
| | | | 368/70 |
| 2011/0268000 A1 | 11/2011 | Kashikar | |
| 2012/0319847 A1* | 12/2012 | Heller | A61B 5/0008 |
| | | | 340/573.1 |
| 2013/0120459 A1* | 5/2013 | Dickinson | G06F 1/163 |
| | | | 345/650 |
| 2013/0247113 A1* | 9/2013 | Zheng | H04N 21/4126 |
| | | | 725/61 |
| 2013/0261405 A1* | 10/2013 | Lee | A61B 5/681 |
| | | | 600/301 |
| 2013/0268897 A1* | 10/2013 | Li | G06F 3/04886 |
| | | | 715/841 |
| 2013/0329532 A1* | 12/2013 | Sorias | G04C 10/00 |
| | | | 368/64 |
| 2014/0070878 A1* | 3/2014 | Kawasaki | G06F 1/3203 |
| | | | 327/543 |
| 2014/0171156 A1* | 6/2014 | Pattikonda | H04M 1/7253 |
| | | | 455/569.1 |
| 2014/0189515 A1* | 7/2014 | Waldman | G06F 3/01 |
| | | | 715/719 |
| 2014/0240243 A1* | 8/2014 | Perala | G06F 3/041 |
| | | | 345/173 |
| 2015/0029829 A1* | 1/2015 | Spadini | G04G 9/0082 |
| | | | 368/226 |
| 2015/0066424 A1* | 3/2015 | Bae | G06F 1/3206 |
| | | | 702/150 |
| 2015/0185815 A1* | 7/2015 | Debates | G06F 1/3209 |
| | | | 713/320 |

FOREIGN PATENT DOCUMENTS

| | | |
|---|---|---|
| CN | 101656795 | 2/2010 |
| CN | 102096446 | 6/2011 |
| CN | 201976157 U | 9/2011 |
| CN | 102823320 | 12/2012 |
| CN | 103237292 | 8/2013 |
| CN | 103279025 | 9/2013 |

OTHER PUBLICATIONS

First Office Action dated Jul. 8, 2016 out of Chinese priority Application No. 201310400189.9 (16 pages including English translation).

* cited by examiner

ELECTRONIC APPARATUS AND INFORMATION PROCESSING METHOD

BACKGROUND

This application claims priority to Chinese patent application No. 201310400189.9 filed on Sep. 5, 2013; and Chinese patent application No. 201410065588.9 filed on Feb. 25, 2014, the entire contents of each are incorporated herein by reference.

This application relates to an electronic apparatus and an information processing method.

Now, wearable electronic apparatus becomes more and more popular. For example, the wearable electronic apparatus in form of glasses or a watch has already appeared. Such electronic apparatus also has various kinds of functions of the electronic apparatus beside wearable form.

However, such wearable electronic apparatus has various defects in power consumption and functionality. Taking a smart watch as example, a processor used by the current usual smart watch is basically a MPU based on Cortex-M3/M4 system on which an operating system is running and which adopts a TFT-LCD display in order for displaying effect. Displaying time of the screen maintaining bright of such watch does not exceed 7 hours. Measure of the usual smart watch is to lighten the screen by a key-press when a user wants to know time, which is like the mobile phone. Thus, experience brought to the user is like the mobile phone instead of the watch. Since the smart watch needs to process a blue-tooth protocol stack and drive the TFT-LCD display now, it needs a relatively strong CPU of which standby power consumption is generally above 30 mW, and thus standby time thereof does not exceed 3 days generally.

Therefore, it is desired to provide a novel and improved electronic apparatus which is able to switch combination of the internal components correspondingly with respect to different using environment to save power consumption while providing improved user's experience.

SUMMARY

According to the embodiments, there provides an electronic apparatus including: a first processing unit for executing an operation of a first type; a second processing unit for executing an operation of a second type, average power consumption of the second processing unit being less than average power consumption of the first processing unit; a sharing unit connected to the first processing unit and the second processing unit and for operating cooperatively with either or both of the first processing unit and the second processing unit selectively according to predetermined conditions; and a fixing unit for fixing relative position relation of the electronic apparatus with the user.

Preferably, the electronic apparatus further includes: a body unit including at least the first processing unit and the second processing unit; wherein, the fixing unit is connected to the body unit and the fixing unit includes at least a fixing status in which the fixing unit is able to be as an annular space or at least a part of an approximate annular space satisfying a first predetermined condition, and the annular space or the approximate annular space is able to surround at periphery of a columnar body satisfying a second predetermined condition.

Preferably, the electronic apparatus includes a first processing subsystem including at least the sharing unit and the first processing unit and a second processing subsystem including at least the sharing unit and the second processing unit, average power consumption of the second processing subsystem is less than average power consumption of the first processing subsystem.

Preferably, the sharing unit includes a display unit connected to the first processing unit and the second processing unit so as to display content output from the first processing unit or the second processing unit selectively according to control of the first processing unit and/or the second processing unit.

Preferably, the first processing subsystem further includes a first display connected to the first processing unit and for displaying the content output from the first processing unit according to the control of the first processing unit, and the second processing subsystem further includes a second display connected to the second processing unit and for displaying the content output from the second processing unit according to the control of the second processing unit, average power consumption of the first display is larger than the average power consumption of the second display.

Preferably, the second display is further connected to the first processing unit, so that the second display displays the content output from the first processing unit according to the control of the first processing unit; or the second processing unit is further connected to the first processing unit, so that the second processing unit receives the content output from the first processing unit and control the second display to display the content received from the first processing unit when processing of the first processing unit is completed.

Preferably, the first display and the second display are provided overlapped in a radial direction of the annular space, and when the first display or the second display provided at inner side of the radial direction of the annular space displays, it is controlled so that light transmittance of the second display or the first display provided at outer side of the radial direction of the annular space is larger than a predetermined threshold.

Preferably, the sharing unit further includes a power supple unit for providing electric power to the respective units of the electronic apparatus and configured to provide the electric power only to the second processing subsystem when a first predetermined condition is satisfied.

Preferably, the power supple unit is provided in the fixing unit.

Preferably, the sharing unit includes a communication unit connected to the first processing unit and the second processing unit and for connecting to network according to control of the first processing unit or the second processing unit according to a predetermined condition.

Preferably, the first processing subsystem includes a first communication unit connected to the first processing unit and for connecting to the network according to the control of the first processing unit and the second processing subsystem includes a second communication unit connected to the second processing unit and for connecting to the network according to the control of the second processing unit, communication distance of the first communication unit is larger than or equal to a predetermined threshold, communication distance of the second communication unit is less than a predetermined threshold, and here, the power consumption of the first communication unit is larger than that of the second communication unit; the first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

Preferably, the first processing subsystem includes the first communication unit and the second communication unit which are connected to the first processing unit and connected to the network according to the control of the first processing unit, the communication distance of the first communication unit is larger than or equal to a predetermined threshold, and the communication distance of the second communication unit is less than a predetermined threshold, here, the power consumption of the first communication unit is larger than that of the second communication unit; the first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

Therefore, the electronic apparatus according to the embodiments can switch combination of internal components correspondingly with respect to different usage environment to save power consumption while providing improved user experience.

Other characteristics and advantages are explained in the subsequent specification, and are obvious partly from the specification and can be understood by implementing the disclosure. The objects and other advantages can be implemented and obtained by structures pointed particularly in the specification, the claims and the accompanying drawings.

BRIEF DESCRIPTION OF THE DRAWINGS

In order to describe the technical solution of the embodiments of the disclosure more clearly, the accompanying drawings necessary for the description of the embodiments are explained simply. The accompanying drawings in the following description are only exemplary embodiments of the disclosure.

DETAILED DESCRIPTION

The respective preferable embodiments are described with reference to the accompanying drawings hereinafter. The description with reference to the accompanying drawings is provided hereinafter to help to understand the exemplified embodiments defined by the claims or the equivalent. It includes various kinds of specific details for helping understanding, and they are only regarded as schematic. Therefore, those skilled in the art would recognize that the embodiments described here can be made various kinds of alternations and modifications without departing from the range and spirit. Further, in order to make the specification more clear and brief, the detailed description on the well-known functions and structures in the art would be omitted.

Hereinafter, the electronic apparatus according to the first embodiment will be described detailed with reference to the accompanying drawings. The electronic apparatus according to the first embodiment may be a wearable electronic apparatus, examples of such apparatus wearable electronic include, but not limited to an electronic apparatus of a watch type, an electronic apparatus of glasses type, an electronic apparatus of a suit type, and so on.

Figure 1:
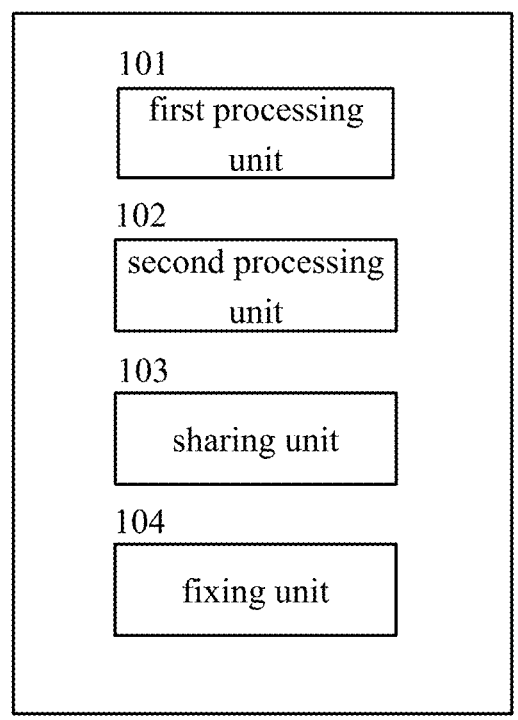
FIG. 1 is a block diagram illustrating a functional configuration of the electronic apparatus according to the first embodiment.

As shown in FIG. 1, the electronic apparatus according to the first embodiment includes at least a first processing unit 101, a second processing unit 102, a sharing unit 103 and a fixing unit 104.

The first processing unit 101 is for executing an operation of a first type. The operation of the first type may include, for example, an operation of network connections (for example, 2G/3G/WiFi network connections and blue-tooth connection); running applications of the electronic apparatus, for example running the applications of the watch if the electronic apparatus is the watch and running the applications of the glasses if the electronic apparatus is the glasses; driving corresponding display units, especially a display unit with good display effect such as the TFT LCD or the like.

The second processing unit 102 is for executing an operation of a second type. The operation of the second type may include, for example, a network connection such as blue-tooth connection with low power consumption; power supply management of the entire system; computing time and date of the system; driving corresponding display units especially the display with low power consumption such as a segment code LCD or the like.

In the electronic apparatus 100, average power consumption of the second processing unit 102 is less than average power consumption of the first processing unit 101. Thus, it can be seen, function of the first processing unit 101 is stronger than that of the second processing unit 102. The first processing unit 101 generally executes operations requiring complex calculation and processing and thus has large average power consumption, and the second processing unit 102 generally executes operations requiring no complex calculation and processing and thus has small average power consumption.

The sharing unit 103 is connected to the first processing unit 101 and the second processing unit 102. Further, the sharing unit 103 is for operating cooperatively with either or both of the first processing unit and the second processing unit selectively according to a predetermined condition, so that the electronic apparatus selectively makes either or both of the first processing unit and the second processing unit to operate cooperatively according to the predetermined condition to function as an independent first processing subsystem and an independent second processing subsystem during operations.

For example, the above-described predetermined condition may include: whether remaining energy of a power supple unit of the electronic apparatus is less than a predetermined threshold, whether a content to be displayed is a content outputted in later time and date or after the applications are executed, whether the electronic apparatus can be connected to the mobile phone or other communication equipment so as to be connected to the network through blue-tooth, whether the electronic apparatus can be connected to the network directly through a 2G/3G communication module, and so on.

The fixing unit 104 is for fixing relative position relation of the electronic apparatus 100 with the user.

The structure of the fixing unit is described detailed with reference to FIGS. 2A to 2E hereinafter.

In the electronic apparatus 100 according to the first embodiment, the electronic apparatus 100 can be divided into a body unit 105 and the fixing unit 104 in perspective of physical structure. The body unit 105 includes at least the first processing unit 101 and the second processing unit 102. The fixing unit 104 is connected to the body unit 105. The sharing unit 103 may be provided in the body unit 105 or in the fixing unit 104 according to different instances.

Figure 2A:
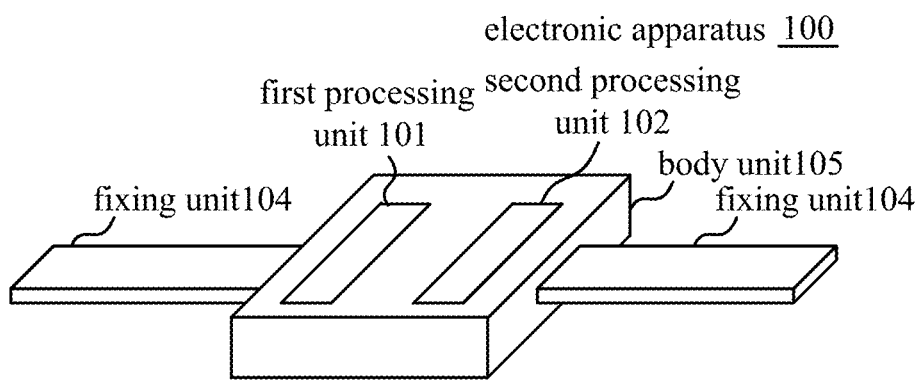
FIG. 2A is a schematic diagram of an exemplary structure of the electronic apparatus shown in FIG. 1.

In particular, as shown in FIG. 2A, the electronic apparatus 100 according to the first embodiment includes the body unit 105 and the fixing unit 104. The fixing unit 104 is connected to the body unit 105. The fixing unit 104 includes at least a fixing status in which the fixing unit 104 is able to be as an annular space or at least a part of an approximate annular space satisfying a first predetermined condition, here, the annular space or the approximate annular space is able to surround at periphery of a columnar body satisfying a second predetermined condition.

Figure 2B:
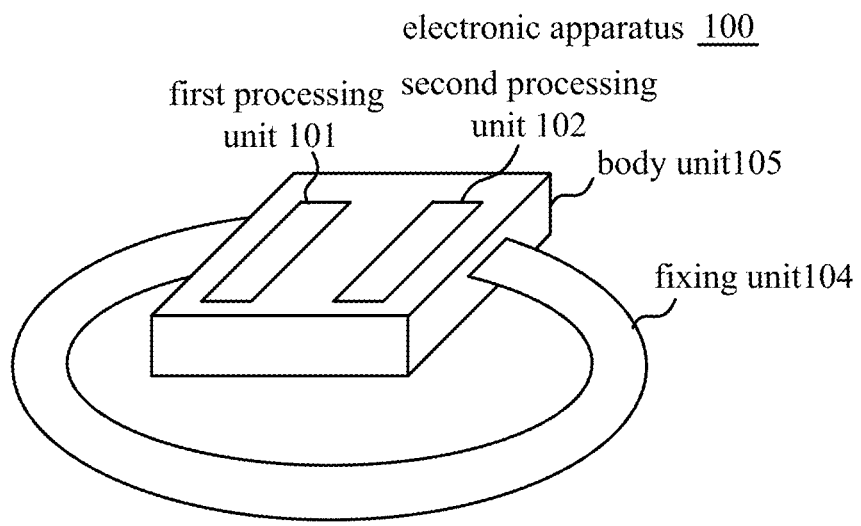
FIG. 2B is a schematic diagram of an exemplary structure of the electronic apparatus shown in FIG. 1.
Figure 2C:
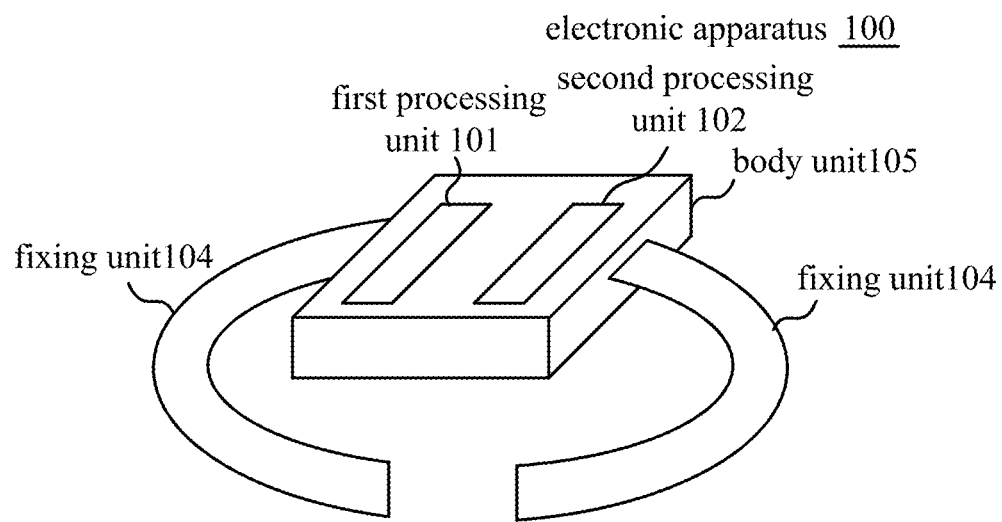
FIG. 2C is a schematic diagram of an exemplary structure of the electronic apparatus shown in FIG. 1.

In particular, FIGS. 2B and 2C illustrate two kinds of fixing status of the fixing unit 104 being connected with the body unit 105 respectively. In a first fixing status as shown in FIG. 2B, the fixing unit 104 forms a loop-locked annular space with the body unit 105, and here, the fixing unit 104 and the body unit 105 constitute a part of the annular space respectively. In a second fixing status as shown in FIG. 2C, the fixing unit 104 forms an approximate annular space having a small opening with the body unit 105, and here, the fixing unit 104 and the body unit 105 constitute a part of the annular space respectively. In a preferable implementation mode, the body unit 105 is a dial plate part of the smart watch and the fixing unit 104 is a watchband part of the smart watch. The annular space or the approximate annular space formed by the body unit 105 and the fixing unit 104 can surround at the periphery of a wrist of the user of the smart watch as the columnar body, and a diameter of the annular space or the approximate annular space is larger than a diameter of the wrist of the user and less than a diameter of a first of the user.

Figure 2D:
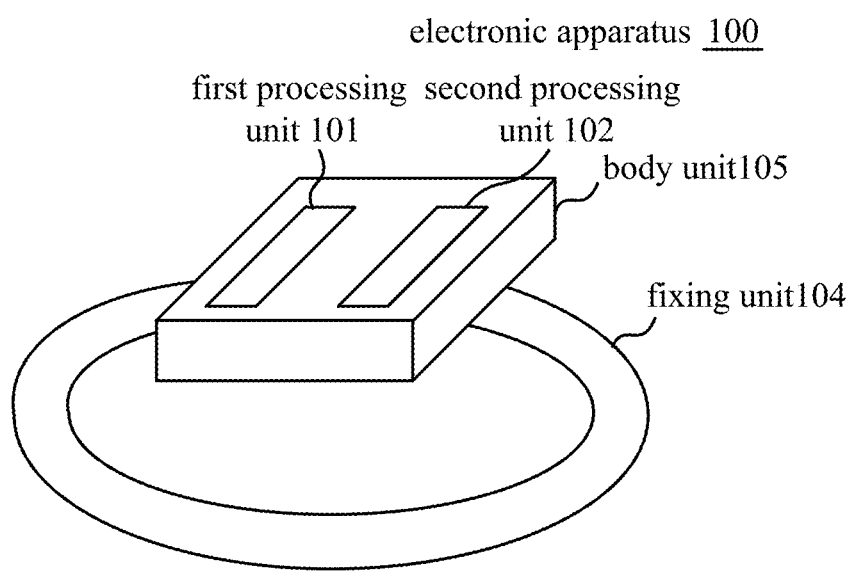
FIG. 2D is a schematic diagram of an exemplary structure of the electronic apparatus shown in FIG. 1.
Figure 2E:
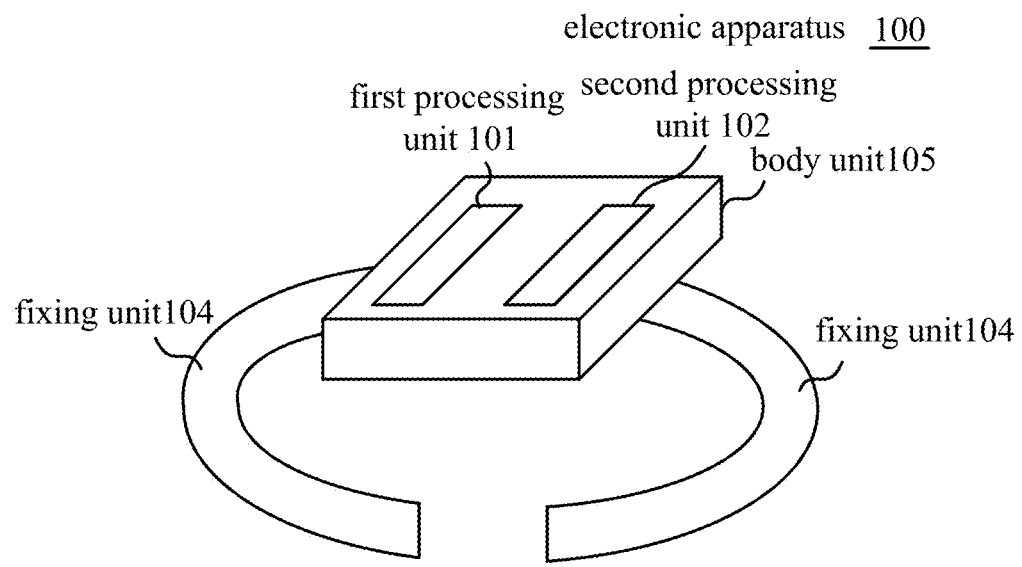
FIG. 2E is a schematic diagram of an exemplary structure of the electronic apparatus shown in FIG. 1.

Further, of course, the annular space or the approximate annular space may also be formed by the fixing unit 104 itself. As shown in FIGS. 2D and 2E, the body unit 105 may be arranged on the fixing unit 104 (i.e., the body unit 105 is attached to the fixing unit 104 in a manner of face contact), so that only the fixing unit 104 itself forms the annular space (FIG. 2D) or the approximate annular space (FIG. 2E) for surrounding the columnar body. The fixing unit 104 is provided with a fixing mechanism (not show) such as a hasp, a snap, a zipper or the like.

Further, as shown in FIGS. 2A to 2E, at least the first processing unit 101 and the second processing unit 102 are provided on the body unit 105.

Figure 3:
FIG. 3 is an effect drawing of one example of the electronic apparatus.

FIG. 3 is an effect drawing illustrating one example of the electronic apparatus 100 according to the first embodiment. In this example, the electronic apparatus 100 is implemented as the watch, and the fixing unit 104 is implemented as the watchband of the watch, and the body unit 105 is implemented as a main body of the watch including a processing unit and a display unit and other functional units.

In one example, the electronic apparatus 100 may include a first processing subsystem and a second processing subsystem. The first processing subsystem includes at least the sharing unit 103 and the first processing unit 101. Further, the second processing subsystem at least includes the sharing unit 103 and the second processing unit 102, and the average power consumption of the second processing subsystem is less than the average power consumption of the first processing subsystem. That is, the sharing unit 103 may be shared by the first processing unit 101 and the second processing unit 102, and constitutes the first processing subsystem and the second processing subsystem with the first processing unit 101 and the second processing unit 103 respectively, so as to adapt for different usage environments.

In particular, in one example, the sharing unit 103 may include a display unit connected to the first processing unit 101 and the second processing unit 102 so as to display the content outputted from the first processing unit 101 or the second processing unit 102 selectively according to the control of the first processing unit 101 and/or the second processing unit 102.

In this example, the display unit is for example a single LCD display connected with both of the first processing unit 101 and the second processing unit 102. The display unit may switch selectively according to which processing unit is operating and outputting the content currently so as to be connected to the processing unit in operation, so as to display the content outputted from the processing unit in operation.

Further, the presently usual smart watch all adopt a single display screen, either a TFT-LCD is adopted for good display effect, or a segment code LCD is adopted for saving power consumption as an electronic watch. Of course, examples of the display are not limited to such examples, other examples of the display may also include an OLED display having a characteristic of high pixel, high resolution and high color contrast, which has good display effect; or other examples of the display may also include an E-ink display having a characteristic of legibility, flexibility, cheap cost and low power consumption.

In case of adopting the TFT-LCD as the display screen, since the power consumption of the TFT-LCD is high, so the TFT-LCD can't keep a status of being lightened, and can only lighten the screen through key-press at the time of needing to view time, view information or the like. Thus, the experience brought to the user is like the mobile phone instead of the watch.

At the time of adopting the segment code LCD, only pre-customized icon can be displayed which only functions as a notice of reminder without implementing push of the content, which results in poor user experience.

Therefore, in another example, the first processing subsystem may further include a first display connected to the first processing unit and for displaying a content outputted from the first processing unit according to the control of the first processing unit, and the second processing subsystem may further include a second display connected to the second processing unit and for displaying a content outputted from the second processing unit according to the control of the second processing unit, and the average power consumption of the first display is larger than the average power consumption of the second display.

In this example, the display unit includes two displays, for example, the first display may be the TFT-LCD display having good display effect, and the second display may be the segment code LCD display having low power consumption. At this time, the electronic apparatus is divided into two processing subsystems, each processing subsystem includes the processing unit and the display unit, so as to operate and display operational content independently.

The electronic apparatus may also include an input unit for inputting various commands, for example, a microphone, a touch unit, a key.

For example, if the user wants to search a restaurant he is interested in; the user may carry out network connection through the first processing subsystem and runs a map application. The user may input name of a restaurant on a map displayed on the TFT-LCD display through the TFT-LCD display having a touch screen function and start to search. Then, the first processing unit is connected to the network and receives map data returned from the server, and then displays search result on the TFT-LCD display, for example, site, telephone number, route of the restaurant or the like. At this time, the user can execute the map search application through the TFT-LCD having good display effect and the first processing unit having strong processing capacity, so as to obtain good user experience.

Further, if remaining energy of the electronic apparatus is not much, the user may carry out implementation of watch function through the second processing subsystem. At this time, the second processing unit having low power consumption can compute time and date of the system, and the segment code LCD display having low power consumption can display the computed time and date, so as to ensure implementation of time function of ordinary watch in case of low energy.

In another example, the above-described second display may also be connected to the first processing unit, so that the second display displays the content outputted from the first processing unit according to the control of the first processing unit.

For example, when the user wants to search the phone number of the restaurant that he is interested in and reserves a seat, the user does not need to use the TFT-LCD display having high power consumption. At this time, the user only needs to input the name of the restaurant through for example a key or a microphone, and then connect the network through the first processing unit and receive the phone number of the restaurant returned from the server. Then, the search result, i.e., the phone number of the restaurant or the like is displayed on the segment code LCD display. At this time, the user may display the phone number on the segment code LCD display all the time until go through the phone number and make reservation, so that it can save power consumption while obtaining good user experience.

In another example, the second processing unit is further connected to the first processing unit, so that the second processing unit receives the content outputted from the first processing unit and controls the second display to displays the content received from the first processing unit when the processing of the first processing unit is completed.

In this example, the second display does not need to be connected to the first processing unit and only the second processing unit needs to be connected to the first processing unit to receive data transmitted from the first processing unit. At this time, data communication can be implemented through a simple connecting type such as a UART, a parallel bus or the like between the first processing unit and the second processing unit. In this case, the first processing unit does not need an additional driving circuit to drive the second display, so as to make design more simple and the cost lower.

In this example, when the processing of the first processing unit is completed, the second processing unit receives the content outputted from the first processing unit and drives the second display so as to display the content received from the first processing unit.

Further, when the electronic apparatus has two display units, the two display units may be provided overlapped or may be provided side by side.

In another example, the first display and the second display are provided overlapped in a radial direction of the annular space, and when the first display or the second display provided at inner side of the radial direction of the annular space displays, it is controlled so that light transmittance of the second display or the first display provided at outer side of the radial direction of the annular space is larger than a predetermined threshold.

In this example, the first display and the second display may be provided overlapped in the radial direction of the annular space formed by the fixing unit. In this case, in order to see the content displayed by the display provided at bottom, it is controlled so that the light transmittance of another display overlapped at the top is larger than the predetermined threshold, that is, in a transparent status when the display overlapped at the bottom displays. Therefore, even if two display units are provided overlapped in the radial direction of the annular space, it may also use the two display units to display the content conveniently.

When two displays are provided overlapped in the radial direction of the annular space, it makes size of the electronic apparatus more compact so that the usage is more convenient while implementing display of two displays.

In one example, the sharing unit 104 may also include a power supple unit for supplying electric power to respective units of the electronic apparatus. In one example, the power supple unit may be provided in the fixing unit. When the power supple unit is provided in the fixing unit, the power supple unit may use a flexible power supple unit which is able to bend according to shape of the fixing unit to be compliant with shape of the annular space formed by the fixing unit. Alternatively, the power supple unit may be provided by grouping a plurality of set of independent sub power supple units. At this time, the respective sub power supple units may be distributed evenly on the fixing unit, so as to be compliant with the shape of the annular space formed by the fixing unit.

When the power supple unit is provided on the fixing unit, the power supple unit may be removed from the body unit, so that the size of the body unit is more compact, which in turn make the size of the electronic apparatus more compact. Further, when the power supple unit is provided on the fixing unit, since the size of the power supple unit is not a problem, the power supple unit having relatively large size and more electric power can be used, so as to make usage time of the electronic apparatus longer.

In one example, the power supple unit is configured to provide electric power only to the second processing subsystem when a first predetermined condition is satisfied. In this example, since the second processing subsystem is a processing subsystem for mainly implementing the function of the watch, in order to ensure stability and persistence of the function of the watch, when the second processing unit detects to find that the remaining energy of the power supple unit is lower than a predetermined threshold, the power supple unit only provides electric power to the second processing subsystem without providing electric power to the first processing subsystem. Since the average power consumption of the second processing subsystem is very low, even less remaining energy can ensure a relatively long usage time of the second processing subsystem, so as to ensure long-term and stable usage of the function of the watch and a function of notification.

Further, in another example, the sharing unit 104 may also include a communication unit connected to the first processing unit and the second processing unit and for connecting to network according to the control of the first processing unit or the second processing unit according to a predetermined condition.

In this example, the sharing unit 104 includes only one communication unit connected to both of the first processing unit 101 and the second processing unit 102. At this time, the communication unit is connected to the network according to the control of the first processing unit 101 or the second processing unit 102 according to the predetermined condition. For example, if the remaining energy of the power supple unit is relatively less, the communication unit is connected to the network according to the control of the first processing unit 101. Or, the communication unit can be periodically connected to the network according to the control of the first processing unit 101 so as to receive a notification. Or, if the user wants to use a sophisticated network application, the communication unit is connected to the network according to the control of the first processing unit 101. The communication unit may include for example a 2G/3G communication module, other future communication module of various mobile communication networks (for example, 4G, 5G or the like), a blue-tooth module, a blue-tooth module having low power consumption or the like.

In another example, the first processing subsystem may include the first communication unit, and the second processing subsystem may include the second communication unit. The first communication unit is connected to the first processing unit 101 and is connected to the network according to the control of the first processing unit 101. The second communication unit is connected to the second processing unit 102 and is connected to the network according to the control of the second processing unit 102. A communication distance of the first communication unit is larger than or equal to a predetermined threshold, a communication distance of the second communication unit is less than a predetermined threshold. Here, the power consumption of the first communication unit is larger than that of the second communication unit.

In this example, for example, the first communication unit may be a 2G/3G communication module, a WiFi communication module or the like, and the second communication unit may be a blue-tooth module, a blue-tooth module having low power consumption or the like. At this time, the first processing subsystem includes the first communication unit, and the second processing subsystem includes the second communication unit.

The communication distance of the first communication module is larger than or equal to a predetermined threshold, for example from tens of meters (for example a WIFI communication module) to thousands of meters (for example, a 2G/3G communication module). At this time, the first communication module can access the network directly via the WiFi communication module or the 2G/3G communication module without help of other electronic apparatus (for example, a mobile phone).

The communication distance of the second communication module is less than a predetermined threshold, for example, ten meters (a blue-tooth module). At this time, the second communication module can be connected to another electronic apparatus (for example, a mobile phone) via the blue-tooth module so as to access the network through the mobile phone.

In one example, the first communication unit stops operating according to the control of the first processing unit when the second communication unit is able to be connected to the network. In this case, if the electronic apparatus such as the smart watch finds that there is a mobile phone that can be paired in the range of the communication distance, the smart phone turns off the first communication module to save electric power after being paired with the mobile phone, and is connected to the network via the mobile phone by the second communication module.

On the other hand, when the second communication unit is not able to be connected to the network, the second communication unit stops operating according to the control of the second processing unit, and the first communication unit is connected to the network according to the control of the first processing unit.

In this case, if the electronic apparatus such as the smart watch finds that there is not a mobile phone that can be paired in the range of the communication distance, the smart phone turns off the second communication module to save electric power, and is connected to the network via the mobile phone by the first communication module. Thus, accessing the network at any time and everywhere of the smart watch is able to be implemented.

In another example, the first processing subsystem includes the first communication unit and the second communication unit which are connected to the first processing unit and connected to the network according to the control of the first processing unit, the communication distance of the first communication unit is larger than or equal to a predetermined threshold, and the communication distance of the second communication unit is less than a predetermined threshold, here, the power consumption of the first communication unit is larger than that of the second communication unit.

In this example, both of the first communication unit and the second communication unit belongs to the first processing subsystem.

Therefore, when the second communication unit is able to be connected to the network, the first communication unit stops operating according to the control of the first processing unit, and when the second communication unit is not able to be connected to the network, the second communication unit stops operating according to the control of the first processing unit, and the first communication unit is connected to the network according to the control of the first processing unit.

In this example, function of network connection is controlled by the first processing subsystem, the second processing subsystem is responsible for only implementation of functions of the watch, for example, viewing time and date.

Hereinafter, one specific implementation mode of the electronic apparatus according to the first embodiment is described with reference to FIG. 4.

Figure 4:
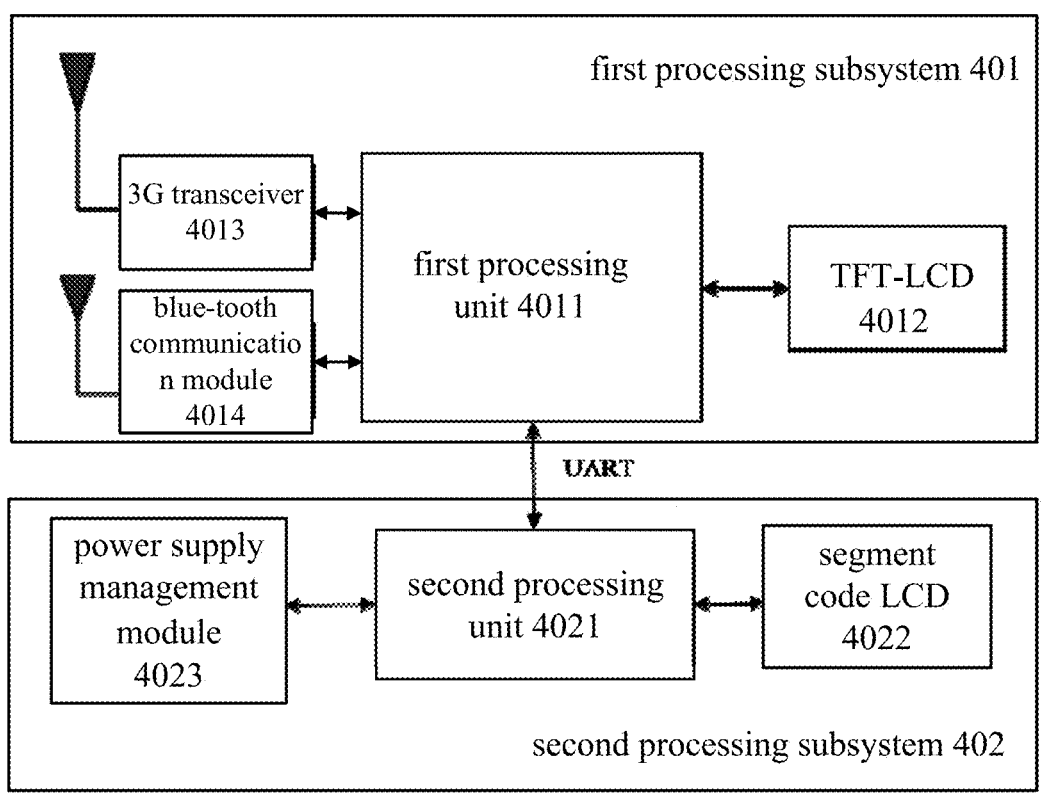
FIG. 4 is a block diagram illustrating a functional configuration of one specific implementation mode of the electronic apparatus according to the first embodiment.

As shown in FIG. 4, the electronic apparatus 400 includes two processing subsystems 401 and 402, the first processing subsystem 401 includes a first processing unit 4011, a TFT-LCD display 4012, a 3G transceiver 4013 and a blue-tooth communication module 4014, and the second processing subsystem 402 includes a second processing unit 4021, a segment code display 4022 and a power supply management module 4023.

In the electronic apparatus 400, the first processing unit 4011 is mainly responsible for: controlling connection of 3G and blue-tooth firstly; running applications of the watch secondly; and driving the TFT-LCD to display thirdly.

The second processing unit 4021 is mainly responsible for: power supply management of the entire system firstly; computing time and date secondly; driving the segment code LCD to display thirdly.

The electronic apparatus 400 is ensured to be able to be used as long as one year after being charged when it is used as the function of the electronic watch.

After the electronic apparatus 400 is turned on, the second processing unit 402 measures electric power of battery using a coulometer. If the electric power is larger than or equal to 20% of total electric power, the first processing subsystem 401 and the second processing subsystem 402 are supplied power supply at the same time by the power supply management module 4023 to ensure the 3G module and the blue-tooth module to operate normally. If the electric power is less than 20%, the power supply management module 4023 only supplies power supply to the second processing subsystem 402, and total power consumption of the second processing unit 4021, the segment code LCD 4022 and the power supply management module 4023 of the processing subsystem is controlled at about 60 uW at this time. It assumes that a battery of 400 mA is adopted, thus, only the second processing subsystem operates, runtime of the system is 400*3.3*0.2/0.06=4400 hours=183 days (it assumes that operating voltage is 3.3V). Thus, if the electric power is plenty, the user is allowed to use the two processing subsystems to let the user enjoy a service of network connection at any time and everywhere; and, if the electric power is not much, the function of the ordinary electronic watch can be ensured, which is unlike many conventional smart watch which has to be charged every 3 days. And it can ensure the segment code screen to be lightened always, so that the time and the notification can be seen only by lowering head by the user.

When the electronic apparatus 400 operates, the first processing unit 4011 detects whether is able to detect the mobile phone by the blue-tooth module 4014. After the mobile phone is detected and the electronic apparatus 400 is paired with the mobile phone through blue-tooth, the electronic apparatus 400 is connected to the network through the 3G module of the mobile phone, and the 3G module 4013 of the electronic apparatus 400 has to be turned off in order for saving electric power; on the other hand, when the electronic apparatus 400 can't detect the mobile phone through blue-tooth, it turns on its own 3G module 4013 to access the network. Thus, the electronic apparatus 400 can be as an accessory of the mobile phone and can have independent network function.

For example, the first processing unit 4011 and the second processing unit 4012 carry out data communication through the UART.

Therefore, the electronic apparatus according to the first embodiments can switch the combination of the internal components correspondingly with respect to the different usage environments to save the power consumption while providing the improved user experience.

Further, based on a same concept, the first embodiment in another aspect provides an information processing method applied in an electronic apparatus including a fixing unit for fixing relative position relation of the electronic apparatus with a user, the information processing method includes: executing an operation of a first type by a first processing unit of the electronic apparatus; executing an operation of a second type by a second processing unit of the electronic apparatus, average power consumption of the second processing unit being less than average power consumption of the first processing unit; operating cooperatively with either or both of the first processing unit and the second processing unit selectively according to a predetermined condition by a sharing unit of the electronic apparatus, wherein the sharing unit is connected to the first processing unit and the second processing unit.

Similarly, the information processing method according to the first embodiments can switch the combination of the internal components of the electronic apparatus correspondingly with respect to the different usage environments to save the power consumption while providing the improved user experience.

As explained in the above, with progressive development of technology, electronic technology has quickly developed such that more and more smart apparatus are applied to life of people, wherein, wearable technique has gotten attention of the people all the time. The wearable technique is applied for intellectualized design of daily apparel, and the developed wearable apparatus may be referred as a "wearable smart apparatus", for example, a watch, glasses or the like, and a part of the wearable apparatus has been commercialized from conceptualization, and new wearable apparatus becomes more.

Now, in order to satisfy usage requirement of the user, most wearable electronic apparatus on the market have more and more functions. In order for the user to use the respective functions of the electronic apparatus in real time, functional modules required to run at the same time of the electronic apparatus are relatively many. It is known that when the electronic apparatus runs the respective functional modules, corresponding operational interfaces are displayed by a display screen generally. For example, in a normal status, the electronic apparatus includes one or more of functional interfaces, and the functional modules corresponding to functional icons in these functional interfaces are all in operational service, so the user can invoke the functions corresponding to the respective functional icons by the functional interfaces at any time. Since the user may switch between different functional interfaces, the electronic apparatus needs to keep all of the functional modules corresponding to the functional icons in the functional interfaces to be in operational status, thus it results in large power consumption of the electronic apparatus, so that the wearable electronic apparatus can't keep a relatively long working time.

The second embodiment provides an information processing method for solving the conventional problem of large power consumption of the wearable electronic apparatus and implementing technical effect of reducing the power consumption of the wearable electronic apparatus.

An information processing method applied in an electronic apparatus, the electronic apparatus includes: a frame structure body including a fixing structure which is able to fix the electronic apparatus on a first operation body; a display unit fixed on the frame structure body and including a display screen; an input unit fixed by the frame structure body and of which a sensing section is able to be positioned at any position on the frame structure body other than the display screen; and a processor connected with the input unit and fixed by the frame structure body and for controlling the electronic apparatus according to parameter obtained by the sensing section of the input unit;

The information processing method including: controlling the electronic apparatus to display a first graphical interface including M first identification objects which are able to feedback working parameters of N functional modules corresponding to the M first identification objects of the electronic apparatus in real time when the electronic apparatus is fixed on the first operation body by the fixing structure, here, M and N being positive integers; obtaining a first manipulation instruction; and controlling the electronic apparatus to display a second graphical interface including P second identification objects for identifying application entries which are able to invoke applications corresponding to the P second identification objects in response to the first manipulation instruction, here, P being a positive integer; wherein, when a trigger operation with respect to an application entry corresponding to the i-th second identification object in the P second identification objects is obtained, an application corresponding to the i-th second identification object is invoked, here, i is a positive integer that is not larger than P.

Preferably, after controlling the electronic apparatus to display the second graphical interface in response to the first manipulation instruction, the method further includes: obtaining the trigger operation with respect to the application entry corresponding to the i-th second identification object in the P second identification objects and invoking the application corresponding to the i-th second identification object.

Preferably, the display screen is a circular screen, and the frame structure body includes a frame main body having a shape matched with the circular screen and for fixing the circular screen, and the second graphical interface is an annular interface, and a first sensing sub-section in the sensing section is provided at a locked structure of the fixing structure, and the first sensing sub-section is a circular sensing section; when the electronic apparatus is fixed on the first operation body by the fixing structure, the circular screen is positioned at a first surface of the first operation body, and the circular sensing section is positioned at a second surface of the first operation body, and the first surface is opposite to the second surface and the circular screen is opposite to the circular sensing section;

After controlling the electronic apparatus to display the second graphical interface in response to the first manipulation instruction, the method further includes: obtaining a track of move operation generated by a move operation carried out on the circular sensing section by the second operation body through the circular sensing section; determining a first position corresponding to the move operation on the circular sensing section according to the track of move operation; determining the second identification object corresponding to the first position according to correspondence relationship between position on the circular sensing section and the second identification object; and controlling to output a prompt information at an identification region in the second graphical interface where the determined second identification object is.

Preferably, the display screen is a circular screen, and the frame structure body includes a frame main body having a shape matched with the circular screen and for fixing the circular screen, and the second graphical interface is an annular interface, and a sensing section of the input unit is provided on the part of the frame main body, and a second sub-sensing section included in sensing section is at a periphery region adjacent to the display screen and the second sub sensing section is an annular sensing area and shares one center with the display screen;

After controlling the electronic apparatus to display the second graphical interface in response to the first manipulation instruction, the method further includes: obtaining a track of move operation generated by a move operation carried out by the second operation body in the annular sensing area through the annular sensing area; adjusting display modes of the second graphical interface according to the track of move operation.

Preferably, adjusting the display modes of the second graphical interface according to the track of move operation is specifically: magnifying the second graphical interface in a first preset proportion according to a first sub-operational track and a second sub-operational track if it determines that the track of move operation includes the first sub-operational track and the second sub-operational track; wherein, if the first sub-operational track and the second sub-operational track are opposite in direction, a distance between the first sub-operational track and the second sub-operational track increases gradually.

Preferably, adjusting the display modes of the second graphical interface according to the track of move operation is specifically: reducing the second graphical interface in a second preset proportion according to a first sub-operational track and a second sub-operational track if it determines that the track of move operation includes the first sub-operational track and the second sub-operational track; wherein, if the first sub-operational track and the second sub-operational track are opposite in direction, a distance between the first sub-operational track and the second sub-operational track decreases gradually.

Preferably, adjusting the display modes of the second graphical interface according to the track of move operation is specifically: controlling the second graphical interface to rotate according to a first sub-operational track and a second sub-operational track if it determines that the track of move operation includes the first sub-operational track and the second sub-operational track and the first sub-operational track and the second sub-operational track are not positioned at a same line.

Preferably, controlling the second graphical interface to rotate according to the first sub-operational track and the second sub-operational track is specifically: deciding whether a first operational direction corresponding to the first sub-operational track is consistent with a second operational direction corresponding to the second sub-operational track; determining the first operational direction as a rotation direction of the second graphical interface when the first operational direction is consistent with the second operational direction and controlling the second graphical interface to rotate according to the rotation direction.

Preferably, determining the first operational direction as the rotation direction of the second graphical interface when the first operational direction is consistent with the second operational direction and controlling the second graphical interface to rotate according to the rotation direction is specifically: determining the first operational direction as the rotation direction of the second graphical interface when the first operational direction is consistent with the second operational direction; determining a first angle formed by a first start point and a first end point of the first sub-operational track with a center of circle and determining a second angle formed by a second start point and a second end point of second first sub-operational track with a center of circle according to the track of move operation; determining an angle of rotation of the second graphical interface according to the first angle and the second angle; and controlling the second graphical interface to rotate according to the angle of rotation and the rotation direction.

An electronic apparatus including: a frame structure body including a fixing structure which is able to fix the electronic apparatus on a first operation body; a display unit fixed on the frame structure body and including a display screen; an input unit fixed by the frame structure body and of which a sensing section is able to be positioned at any position on the frame structure body other than the display screen; and a processor connected with the input unit and fixed by the frame structure body and for controlling the electronic apparatus according to parameter obtained by the sensing section of the input unit;

The electronic apparatus further includes: a control unit for controlling the electronic apparatus to display a first graphical interface including M first identification objects which are able to feedback working parameters of N functional modules corresponding to the M first identification objects of the electronic apparatus in real time when the electronic apparatus is fixed on the first operation body by the fixing structure, here, M and N being positive integers; a first acquiring unit for obtaining a first manipulation instruction; a response unit for controlling the electronic apparatus to display a second graphical interface including P second identification objects for identifying application entries which are able to invoke applications corresponding to the P second identification objects in response to the first manipulation instruction, here, P is a positive integer; wherein, when a trigger operation with respect to an application entry corresponding to the i-th second identification object in the P second identification objects is obtained, an application corresponding to the i-th second identification object is invoked, here, i is a positive integer that is not larger than P.

Preferably, the electronic apparatus further includes a third acquiring unit for obtaining a trigger operation with respect to an application entry corresponding to the i-th second identification object in the P second identification objects and invoking an application corresponding to the i-th second identification object.

Preferably, the display screen is a circular screen, and the frame structure body includes a frame main body having a shape matched with the circular screen and for fixing the circular screen, and the second graphical interface is an annular interface, and a first sensing sub-section in the sensing section is provided at a locked structure of the fixing structure, and the first sensing sub-section is a circular sensing section; when the electronic apparatus is fixed on the first operation body by the fixing structure, the circular screen is positioned at a first surface of the first operation body, and the circular sensing section is positioned at a second surface of the first operation body, and the first surface is opposite to the second surface and the circular screen is opposite to the circular sensing section;

The electronic apparatus further includes: a third acquiring unit for obtaining a track of move operation generated by a move operation carried out on the circular sensing section by the second operation body through the circular sensing section; a first determining unit for determining a first position corresponding to the move operation on the circular sensing section according to the track of move operation; a second determining unit for determining the second identification object corresponding to the first position according to correspondence relationship between position on the circular sensing section and the second identification object; and an output unit for controlling to output a prompt information at an identification region in the second graphical interface where the determined second identification object is.

Preferably, the display screen is a circular screen, and the frame structure body includes a frame main body having a shape matched with the circular screen and for fixing the circular screen, and the second graphical interface is an annular interface, and a sensing section of the input unit is provided on the part of the frame main body, and a second sub-sensing section included in sensing section is at a periphery region adjacent to the display screen and the second sub sensing section is an annular sensing area and shares one center with the display screen;

The electronic apparatus further includes: a fourth acquiring unit for obtaining a track of move operation generated by a move operation carried out by the second operation body in the annular sensing area through the annular sensing area; an adjusting unit for adjusting display modes of the second graphical interface according to the track of move operation.

Preferably, the adjusting unit specifically for: magnifying the second graphical interface in a first preset proportion according to a first sub-operational track and a second sub-operational track if it determines that the track of move operation includes the first sub-operational track and the second sub-operational track; wherein, if the first sub-operational track and the second sub-operational track are opposite in direction, a distance between the first sub-operational track and the second sub-operational track increases gradually.

Preferably, the adjusting unit specifically for: reducing the second graphical interface in a second preset proportion according to a first sub-operational track and a second sub-operational track if it determines that the track of move operation includes the first sub-operational track and the second sub-operational track; wherein, if the first sub-operational track and the second sub-operational track are opposite in direction, a distance between the first sub-operational track and the second sub-operational track decreases gradually.

Preferably, the adjusting unit specifically for: controlling the second graphical interface to rotate according to a first sub-operational track and a second sub-operational track if it determines that the track of move operation includes the first sub-operational track and the second sub-operational track and the first sub-operational track and the second sub-operational track are not positioned at a same line.

Preferably, the adjusting unit being specifically for controlling the second graphical interface to rotate according to the first sub-operational track and the second sub-operational track is specifically: deciding whether a first operational direction corresponding to the first sub-operational track is consistent with a second operational direction corresponding to the second sub-operational track; determining the first operational direction as rotation direction of the second graphical interface when the first operational direction is consistent with the second operational direction and controlling the second graphical interface to rotate according to the rotation direction.

Preferably, the adjusting module being specifically for determining the first operational direction as the rotation direction of the second graphical interface when the first operational direction is consistent with the second operational direction and controlling the second graphical interface to rotate according to the rotation direction is specifically: determining the first operational direction as the rotation direction of the second graphical interface when the first operational direction is consistent with the second operational direction; determining a first angle formed by a first start point and a first end point of the first sub-operational track with a center of circle and determining a second angle formed by a second start point and a second end point of second first sub-operational track with a center of circle according to the track of move operation; determining an angle of rotation of the second graphical interface according to the first angle and the second angle; and controlling the second graphical interface to rotate according to the angle of rotation and the rotation direction.

In the second embodiment, since both of the display unit and the input unit are fixed on the frame structure body, when the electronic apparatus is fixed on the first operation body and display the first graphical interface by the display unit, the user can know current status of the parameters of the electronic apparatus conveniently through the working parameters of N functional modules corresponding thereto feedback by the M first identification objects, for example, electric power, time, signal or the like. That is, when the electronic apparatus displays the M first identification objects, only operational modules corresponding to the M first identification objects needs to run, so the electronic apparatus can be in a status of low power consumption. And, when the first operational instruction is obtained, the electronic apparatus is controlled to include the second graphical interface including the P second identification objects, and at this time, the electronic apparatus only needs to run the functional modules corresponding to the P second identification objects without running the N functional modules corresponding to the M first identification objects any longer. Thus, when the electronic apparatus switches between the first graphical interface and the second graphical interface, only the functional modules corresponding to the identification objects in the current graphical interface needs to run, so that the power consumption of the electronic apparatus is reduced and usage time of the electronic apparatus is extended.

Hereinafter, the information processing method and the electronic apparatus according to the second embodiment will be described detailed with reference to the accompanying drawings.

The second embodiment provides an information processing method applied in an electronic apparatus, the electronic apparatus includes: a frame structure body including a fixing structure which is able to fix the electronic apparatus on a first operation body; a display unit fixed on the frame structure body and including a display screen; an input unit fixed by the frame structure body and of which a sensing section is able to be positioned at any position on the frame structure body other than the display screen; and a processor connected with the input unit and fixed by the frame structure body and for controlling the electronic apparatus according to parameter obtained by the sensing section of the input unit;

The information processing method includes: controlling the electronic apparatus to display a first graphical interface including M first identification objects which are able to feedback working parameters of N functional modules corresponding to the M first identification objects of the electronic apparatus in real time when the electronic apparatus is fixed on the first operation body by the fixing structure, here, M and N being positive integers; obtaining a first manipulation instruction; and controlling the electronic apparatus to display a second graphical interface including P second identification objects for identifying application entries which are able to invoke applications corresponding to the P second identification objects in response to the first manipulation instruction, here, P being a positive integer; wherein, when a trigger operation with respect to an application entry corresponding to the i-th second identification object in the P second identification objects is obtained, an application corresponding to the i-th second identification object is invoked, here, i is a positive integer that is not larger than P.

In the second embodiment, since both of the display unit and the input unit are fixed on the frame structure body, when the electronic apparatus is fixed on the first operation body and display the first graphical interface by the display unit, the user can know current status of the parameter of the electronic apparatus conveniently through the working parameter of N functional modules corresponding thereto feedback by the M first identification objects, for example, electric power, time, signal or the like. That is, when the electronic apparatus displays the M first identification objects, only operational modules corresponding to the M first identification objects needs to run, so the electronic apparatus can be in a status of low power consumption. And, when the first operational instruction is obtained, the electronic apparatus is controlled to include the second graphical interface including the P second identification objects, and at this time, the electronic apparatus only needs to run the functional modules corresponding to the P second identification objects without running the N functional modules corresponding to the M first identification objects any longer. Thus, when the electronic apparatus switches between the first graphical interface and the second graphical interface, only the functional modules corresponding to the identification objects in the current graphical interface needs to run, so that the power consumption of the electronic apparatus is reduced and the usage time of the electronic apparatus is extended.

Figure 5:
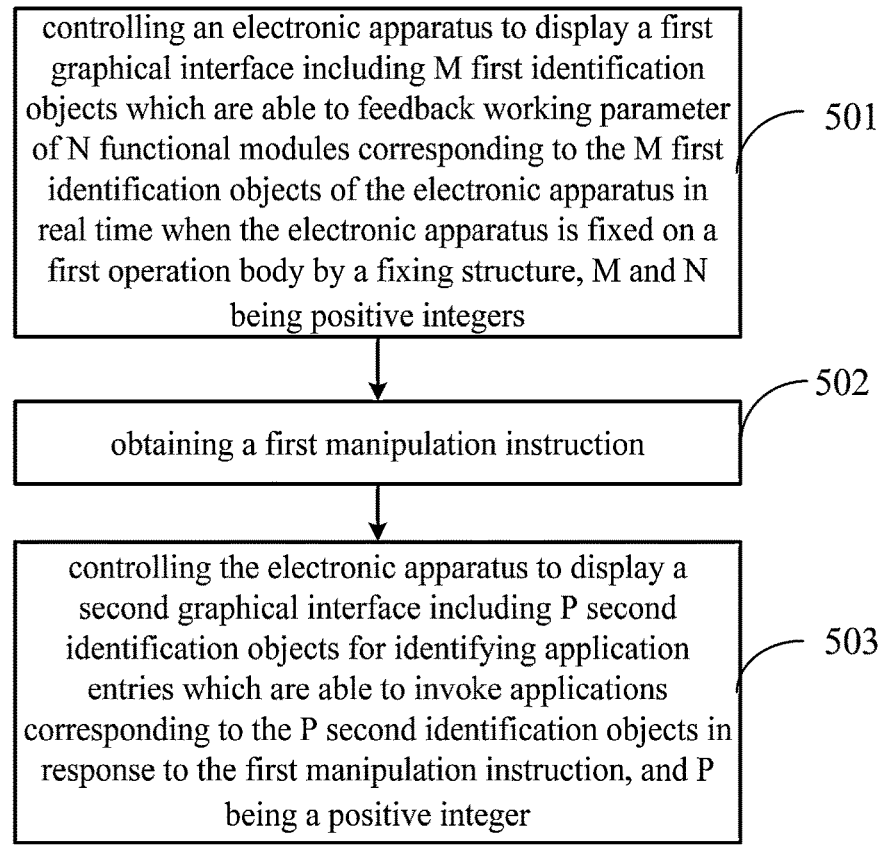
FIG. 5 is a main flow chart of an information processing method in a second embodiment.

With reference to FIG. 5, the second embodiment provides an information processing method applied in an electronic apparatus, the electronic apparatus may include: a frame structure body including a fixing structure which is able to fix the electronic apparatus on a first operation body; a display unit fixed on the frame structure body and including a display screen; an input unit fixed by the frame structure body and of which a sensing section is able to be positioned at any position on the frame structure body other than the display screen; and a processor connected with the input unit and fixed by the frame structure body and for controlling the electronic apparatus according to parameter obtained by the sensing section of the input unit; The main flow of the method is as follows:

Step 501: controlling the electronic apparatus to display a first graphical interface including M first identification objects which are able to feedback working parameters of N functional modules corresponding to the M first identification objects of the electronic apparatus in real time when the electronic apparatus is fixed on the first operation body by the fixing structure, here, M and N being positive integers.

In the second embodiment, the electronic apparatus may be a wearable electronic apparatus, for example, a smart watch. The fixing structure may be a watch buckle of the watch, and the first operation body may be an arm of the user, then the watch can be fixed to the arm of the user by the watch buckle.

Figure 6:
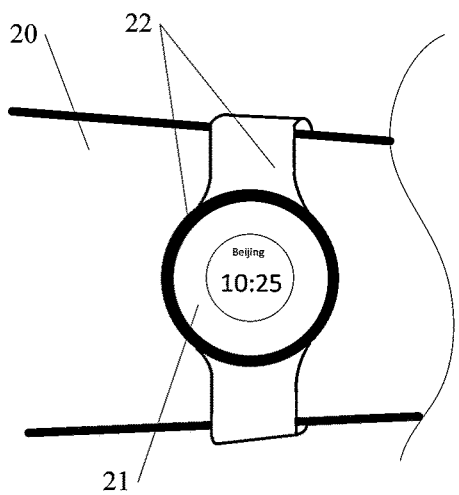
FIG. 6 is a schematic diagram of a structure of the wearable electronic apparatus in the second embodiment.

With reference to FIG. 6, number 20 represents the first operation body, which takes the arm of the user as example, number 21 represents the display unit, number 22 represents the sensing section of the input unit, here, and the display unit displays the first graphical interface.

In the second embodiment, the first graphical interface may be regarded as original interface of the electronic apparatus, and the original interface may provide basic desktop information to the user, for example, time and date or the like. The M first identification objects displayed in the first graphical interface may correspond to display identification of time, electric power, apparatus signal or the like. Or the first graphical interface may also be a time dial plate displayed by the display unit of the electronic apparatus. For example, the time dial plate may be specifically a mechanical dial plate, the display unit may be a display screen provided above it with adjustable transparency, the transparency of the display screen may be 100 degree, i.e., in a transparent status when the first graphical interface is display, so that the user may see the time dial plate through the display screen.

Preferably, in the second embodiment, the M first identification objects correspond to the N functional modules, the functional modules are modules to be run for implementing a certain function of the electronic apparatus, for example, a timing module, an output module or the like. Further, the M first identification objects are able to feedback the working parameters of the N functional modules in real time. For example, the functional module corresponding to the identification object of electric power is a functional module of power supply, and the working parameter thereof may include parameter of remaining energy or the like. Wherein M may be equal to N, that is, the first identification object may correspond to the functional modules one by one, or M is not equal to N, for example, one working parameter feedback by one first identification object may be a result of commonly running of a plurality of functional modules, that is, one first identification object may correspond to a plurality of functional modules.

In the second embodiment, since the electronic apparatus is able to display the first graphical interface when the electronic apparatus is fixed to the first operation body, the user can know the working parameter of the N functional modules at any time through the M first identification objects, so that the user can understand current status of the electronic apparatus timely, for example, can know whether there is case of low electric power, better signal or the like in the electronic apparatus in time, so as to carry out corresponding operations. The electronic apparatus of the second embodiment provides the user a relatively intuitive display effect, so as to facilitate the user to view and carry out later processing.

Step 502: obtaining a first manipulation instruction.

In the second embodiment, the first manipulation instruction may be an instruction generated according to a touch control operation by the electronic apparatus after the touch control operation is obtained by the sensing section of the input unit. For example, the user carries out a click operation on the sensing section by a finger, which is equivalent to the user carrying out the touch control operation, and the electronic apparatus may generate the first manipulation instruction according to the click operation.

Or, the first manipulation instruction may also be a manipulation instruction generated by triggering the electronic apparatus by special conditions. For example, when other modules than the N functional modules in the electronic apparatus start to run, the first manipulation instruction is triggered, so that the electronic apparatus is made to execute corresponding function according to the first manipulation instruction. For example, display interface or icon or the like corresponding to the functional module run newly is displayed.

Step 503: controlling the electronic apparatus to display a second graphical interface including P second identification objects for identifying application entries which are able to invoke applications corresponding to the P second identification objects in response to the first manipulation instruction, here, P is a positive integer;

Wherein, when a trigger operation with respect to an application entry corresponding to the i-th second identification object in the P second identification objects is obtained, an application corresponding to the i-th second identification object is invoked, here, i is a positive integer that is not larger than P.

In the second embodiment, when the electronic apparatus displays the second graphical interface in response to the first manipulation instruction, the display unit may have two kinds of display modes. Wherein the first kind of display mode is displaying the first graphical interface and the second graphical interface simultaneously in the display unit. For example, a display region occupied by the second graphical interface may be positioned at a periphery region of the display region occupied by the first graphical interface, and the user may still watch the M first identification objects through the first graphical interface at this time, and the electronic apparatus will run functional modules corresponding to the P second identification objects and the N functional modules corresponding to the M first identification objects at the same time. Wherein the second kind of display mode is displaying only the second graphical interface in the display unit. When the electronic apparatus responds to the first manipulation instruction, the first graphical interface is prohibited from displaying, only the second graphical interface is displayed in the display unit, and at this time, the electronic apparatus may only run operational modules corresponding to the P second identification objects, so as to make the electronic apparatus to display the second graphical interface in a status of low power consumption. Generally, in the second kind of display mode, since the first graphical interface is prohibited from displaying, the user may not understand the parameter information feedback by the M first identification objects in real time, therefore, one or more of the M first identification objects are displayed in the display unit in a small proportion. For example, small identifications corresponding to time, electric power and signal are displayed in a region of upper right corner of the display unit respectively, so as to provide feedback information to the user in real time. Then, the electronic apparatus only run the functional modules corresponding to the displayed identification objects without running all functional modules, so as to make the electronic apparatus to operate in a status of low power consumption.

Preferably, in the second embodiment, the P second identification objects may be identifications of applications arranged and displayed in the second graphical interface in a preset rule. For example, if a shape of the second graphical interface is a ring shape, the second identification object may be distributed evenly in a corresponding annular region.

In the second embodiment, after controlling the electronic apparatus to display the second graphical interface in response to the first manipulation instruction, the method further includes: obtaining a trigger operation with respect to an application entry corresponding to the i-th the second identification object in the P second identification object, and invoking an application corresponding to the i-th second identification object.

Since the P second identification objects may be for identifying an application entry which is able to invoke an application corresponding to the P second identification objects, therefore, when the trigger operation with respect to a certain identification object in the P second identification objects is obtained, the electronic apparatus can invoke the application corresponding to the second identification object, so as to facilitate the user to user the application.

Figure 7:
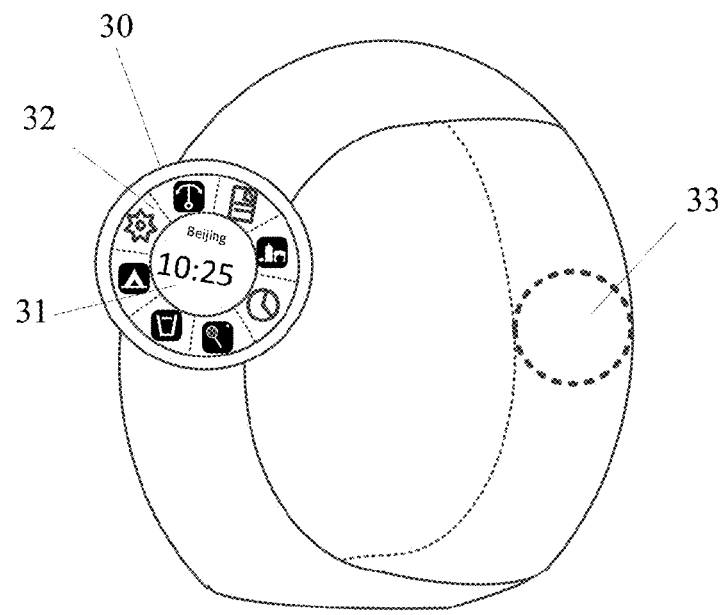
FIG. 7 is a schematic diagram of a first sensing sub-section in the electronic apparatus in the second embodiment.

Preferably, in the second embodiment, the display screen is a circular screen, and the frame structure body includes a frame main body having a shape matched with the circular screen and for fixing the circular screen, and the second graphical interface is an annular interface, and a first sensing sub-section in the sensing section is provided at a locked structure of the fixing structure, and the first sensing sub-section is a circular sensing section. When the electronic apparatus is fixed on the first operation body by fixing structure, the circular screen is positioned at a first surface of the first operation body, and the circular sensing section is positioned at a second surface of the first operation body, and the first surface is opposite to the second surface and the circular screen is opposite to the circular sensing section;

With reference to FIG. 7, number 30 represents the display screen, number 31 represents the first graphical interface in the display screen, number 32 represents the second graphical interface displayed in the display screen, number 33 represents the first sensing sub-section, wherein, the first sensing sub-section is the circular sensing section, and the first graphical interface and the second graphical interface are displayed in the circular screen, that is, the display unit is in the first kind of display mode.

Preferably, in the second embodiment, taking the electronic apparatus having the above-described structure as example, after controlling the electronic apparatus to display the second graphical interface in response to the first manipulation instruction, the method may also include: obtaining a track of move operation generated by a move operation carried out on the circular sensing section by the second operation body through the circular sensing section; determining a first position corresponding to the move operation on the circular sensing section according to the track of move operation; determining the second identification object corresponding to the first position according to correspondence relationship between position on the circular sensing section and the second identification object; and controlling to output prompt information at an identification region in the second graphical interface where the determined second identification object is.

In the second embodiment, the second operation body may be for example a finger of the user, or for example a capacitive pent, or may also be other operational body. For example, the electronic apparatus is the smart watch, when the smart watch is worn on the wrist of left hand of the user, the user may operate the smart watch by a finger of right hand, for example, providing alarming bell.

Preferably, in the second embodiment, when the second operation body carries out the move operation on the circular sensing section, the electronic apparatus can obtain the track of move operation corresponding to the move operation, to determine the first position corresponding to the second operation body on the circular sensing section according to the track of move operation. For example, when the user carries out the move operation on the circular sensing section of the second surface by a finger, the electronic apparatus may know a position to which the finger of the user moves currently according to the track of move operation.

In the second embodiment, when the electronic apparatus is fixed on the first operation body, since the circular sensing section is on a second surface of the first operation body, the second image is on a first surface of the first operation body, and the first surface is opposite to the second surface, so the user can't watch the circular screen and the circular sensing section simultaneously. Therefore, correspondence relationship between the position on the circular sensing section and the second identification object may be set in advance, to associate positions on the circular screen and the circular sensing section.

For example, when the second graphical interface is an annular interface, the annular interface is divided evenly into P identification regions, and each identification region can display one second identification object. Meanwhile, the circular sensing section positioned at the second surface has P sensing regions divided with a center of circle as center. Wherein, the P sensing regions are corresponding to the P second identification objects, so that when the second operation body is determined to be at the first position in the circular sensing section through the track of move operation, the sensing region corresponding to the first position may be determined, so that the second identification object corresponding to the first position can be determined according to the correspondence relationship between the sensing region and the second identification object, and the second identification object is controlled to output prompt information on the identification region where the second graphical interface is.

Wherein, types of the prompt information may be various, and the disclosure does not make specific limitation. For example, one potential mode of outputting the prompt information is: controlling the identification region to display a preset color for prompt.

In the second embodiment, since the first sensing sub-section, i.e., the circular sensing section is provided on an opposite surface to the surface of the circular screen, and when the circular sensing section obtains the track of move operation, the second identification object corresponding to the first position where the second operation body is can be determined, that is, the second identification object selected currently can be determined. Therefore, the user may control the second graphical interface by an operation carried out in the circular sensing section.

For example, when the user faces the first surface, the circular sensing section on the second surface can't be viewed at this time, if the user carries out a slide operation on the second surface by a finger, in the procedure of sliding of the finger, the identification region where the second identification object corresponding to the position at which the finger is would present a certain selected color, for example blue, to indicate that the current slide operation selects the second identification object in the identification region. If the finger continues to move to other positions, the corresponding identification region is displayed as blue, and the identification region displayed as blue previously is prohibited from being displayed as blue and restores an original color. From viewing angle of the user, along with the movement of the finger in the circular sensing section, the blue identification region in the display unit moves correspondingly.

Figure 8:
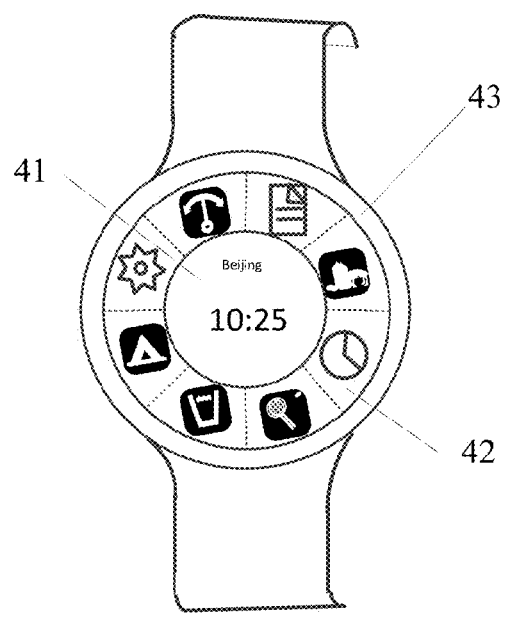
FIG. 8 is a schematic diagram of a second sensing sub-section in the electronic apparatus in the second embodiment.

In the second embodiment, the display screen is a circular screen, and the frame structure body includes a frame main body having a shape matched with the circular screen and for fixing the circular screen, and the second graphical interface is an annular interface, and a sensing section of the input unit is provided on the part of the frame main body, and a second sub-sensing section included in sensing section is at a periphery region adjacent to the display screen and the second sub sensing section is an annular sensing area and shares one center with the display screen. With reference to FIG. 8, number 41 represents the first graphical interface, number 42 represents the second graphical interface, the second graphical interface is an annular interface and the first graphical interface and the second graphical interface have same center of circle, number 43 represents the second sub sensing section.

Preferably, in the second embodiment, taking the electronic apparatus having the above-described structure as example, after controlling the electronic apparatus to display the second graphical interface in response to the first manipulation instruction, the method may also include: obtaining a track of move operation generated by a move operation carried out by the second operation body in the annular sensing area through the annular sensing area; adjusting display modes of the second graphical interface according to the track of move operation.

In the second embodiment, since the annular sensing area is at the periphery region adjacent to the display screen, that is, the user is able to view the annular sensing area and display screen simultaneously, when the user carries out the move operation through the annular sensing area at the periphery region, the electronic apparatus can obtain the track of move operation corresponding to the move operation, so as to implement adjustment of the display interface in the circular screen, for example, magnification, reduction, rotation or the like.

Preferably, in the second embodiment, adjusting the display modes of the second graphical interface according to the track of move operation includes at least three kinds of adjusting method.

Wherein the first kind of adjusting method is specifically: magnifying the second graphical interface in a first preset proportion according to a first sub-operational track and a second sub-operational track if it determines that the track of move operation includes the first sub-operational track and the second sub-operational track; wherein, if the first sub-operational track and the second sub-operational track are opposite in direction, a distance between the first sub-operational track and the second sub-operational track increases gradually.

Preferably, in the second embodiment, the distance between the first sub-operational track and the second sub-operational track may include two kinds of cases, wherein, the first kind may be a first distance in a direction which is parallel to a direction of move operation corresponding to the move operation; the second kind may be a second distance in a direction which is perpendicular to the direction of move operation corresponding to the move operation. Thus, when it determines that the track of move operation includes two sub tracks of operation, the first distance and the second distance between the first sub-operational track and the second sub-operational track are further determined, so as to decide effect of the move operation, for example, increasing or decreasing gradually according to the first distance and the second distance. Specific decision method may be: deciding whether the first distance is less than a preset distance which may be an offset distance generated according to practical operating procedure of the user, for example, when the user draws a line, there is always a part of track deviating from the line, however, if the offset distance is within a certain range, it is regarded as a line direction generally, that is, the preset distance may be a maximum value of the allowed deviation. For example, the preset distance is 0.5 cm, when the first distance does not exceed the preset distance, the directions of the two sub tracks of operation are regarded as in a same line, that is, the move operation is an operation for magnifying or reducing the second graphical interface. If the preset distance is exceeded, the move operation may be operation for rotating the second graphical interface.

Figure 9A:
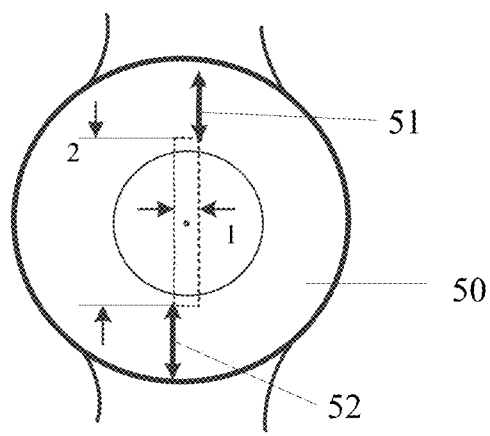
FIG. 9A is a schematic diagram of determining a distance between sub-operational tracks in the second embodiment.

With reference to FIG. 9A, number 50 represents the annular sensing area, number 51 represents a direction corresponding to the first sub-operational track, number 52 represents a direction corresponding to the second sub-operational track, two arrows represent directions that the move operation moves likely, wherein, a pitch between a first group of single arrow labeled as 1 means the first distance, a pitch between a second group of single arrow labeled as 2 means the second distance. If the preset distance is 0.5 cm, when it determines that the first distance does not exceed 0.5 cm, if the second distance between the first sub-operational track and the second sub-operational track increases gradually, it can determine that the move operation is a magnifying operation. Or if the second distance between the first sub-operational track and the second sub-operational track decreases gradually, it can determine that the move operation is a reducing operation. Or if the first distance is larger than 0.5 cm, it can determine that the move operation is a rotating operation.

That is, in the second embodiment, when the display unit displays the second graphical interface and the track of move operation is determined as including the first sub-operational track and the second sub-operational track, if the first sub-operational track and the second sub-operational track are opposite in direction, the distance between the first sub-operational track and the second sub-operational track increases gradually, and the move operation can control the second graphical interface to be magnified according to a first preset proportion. For example, when a forefinger and a thumb of the user are at relative positions in the annular sensing area respectively, if the user controls the forefinger and the thumb to slide away from the center of circle at the same time, the move operation can control the second graphical interface to be magnified according to the first preset proportion.

Figure 9B:
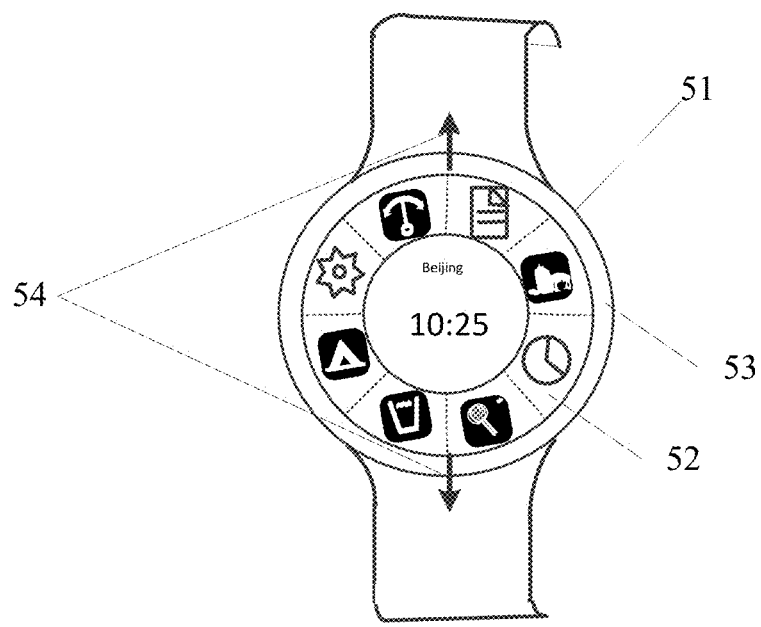
FIG. 9B is a schematic diagram of magnifying a second graphical interface by a move operation in the second embodiment.

For example, with reference to FIG. 9B, number 51 represents the circular screen, number 52 represents the second graphical interface, number 53 represents the second sub sensing section, i.e., the annular sensing area, number 54 represents two sub tracks of operation with opposite directions included in the track of move operation, i.e., the first sub-operational track and the second sub-operational track, and a direction of movement of the track of move operation is a direction away from the center of circle, which indicates that the move operation is a magnifying operation of the second graphical interface. The second graphical interface displayed after in response to the move operation would be an interface magnified according to the first preset proportion.

Figure 9C:
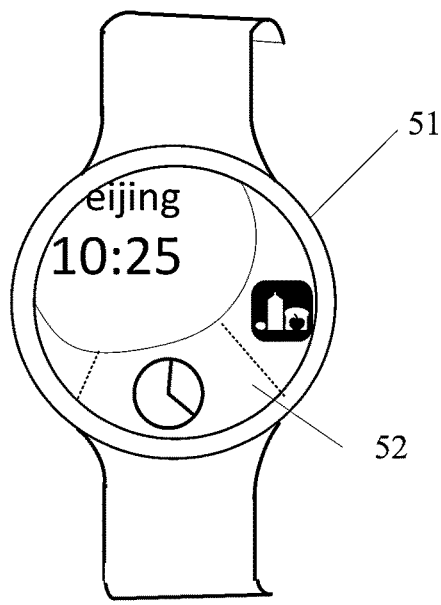
FIG. 9C is a schematic diagram of magnifying a second graphical interface by a move operation in the second embodiment.

For example, with reference to FIG. 9C, wherein, number 51 represents the circular screen, number 52 represents the second graphical interface magnified according to a preset proportion, at this time, the user can view the at least one second identification object displayed in the circular screen clearly.

Preferably, in the second embodiment, the second kind of adjusting method for adjusting the display mode of the second graphical interface according to the track of move operation is: reducing the second graphical interface according to a second preset proportion according to the first sub-operational track and the second sub-operational track if it determines that the track of move operation includes the first sub-operational track and the second sub-operational track. Wherein, if the first sub-operational track and the second sub-operational track are opposite in direction, a distance between the first sub-operational track and the second sub-operational track decreases gradually.

That is, in the second embodiment, if the first sub-operational track and the second sub-operational track are opposite in direction, and the distance between the first sub-operational track and the second sub-operational track decreases gradually, it can determine that the move operation is an adjusting operation for reducing the display interface in the circular screen. Wherein, as to the procedure of determining the change in the distance between the first sub-operational track and the second sub-operational track, it is described detailed in the first kind of adjusting method, and it is not described here.

Figure 10:
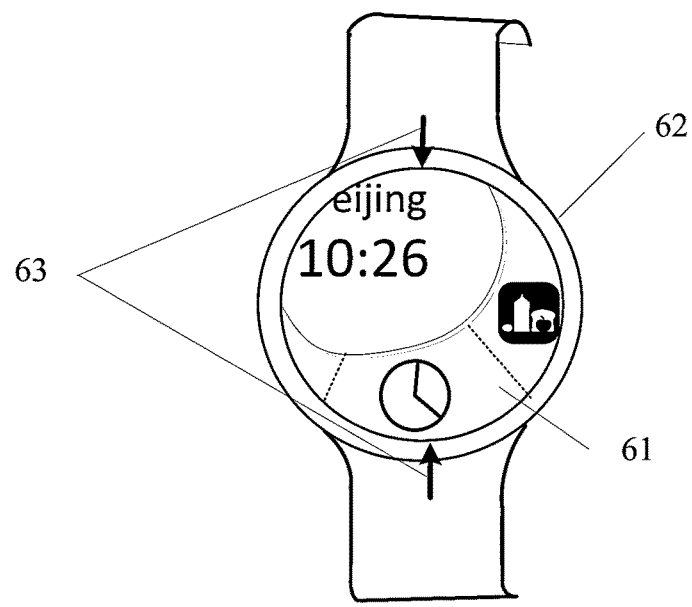
FIG. 10 is a schematic diagram of a track of move operation corresponding to a move operation for reducing the second graphical interface in the second embodiment.

For example, with reference to FIG. 10, number 61 represents the second graphical interface, here the second graphical interface is in a magnified display status, number 62 represents the annular sensing area, and number 63 represents the track of move operation including two sub-operational tracks having opposite directions. Wherein, the two sub tracks of operation and the center of circle are positioned in a same line, and the movement direction of the move operation is a direction closer to the center of circle as the direction of arrow in the drawing.

It can determine that the move operation is an adjusting operation for reducing the second graphical interface according to the second preset proportion at this time. For example, the second graphical interface may be reduced to an original normal display proportion.

Preferably, in the second embodiment, the third kind of the adjusting method of adjusting the display modes of the second graphical interface according to the track of move operation is: controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

Preferably, in the second embodiment, controlling the second graphical interface to rotate according to the first sub-operational track and the second sub-operational track may be specifically: deciding whether a first operational direction corresponding to the first sub-operational track is consistent with a second operational direction corresponding to the second sub-operational track; determining the first operational direction as a rotation direction of the second graphical interface when the first operational direction is consistent with the second operational direction and controlling the second graphical interface to rotate according to the rotation direction.

Figure 11A:
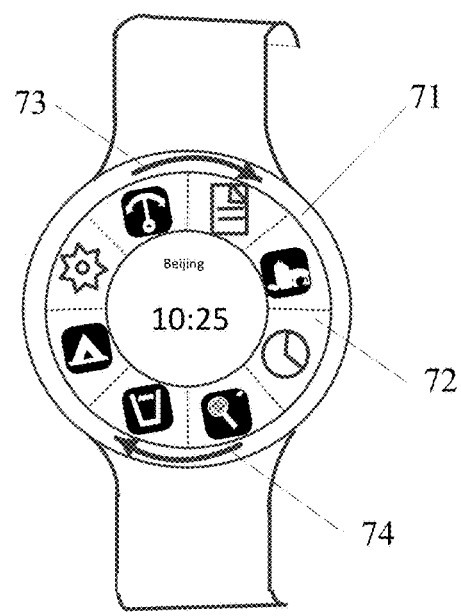
FIG. 11A is a schematic diagram of rotating the second graphical interface by a move operation in the second embodiment.
Figure 11B:
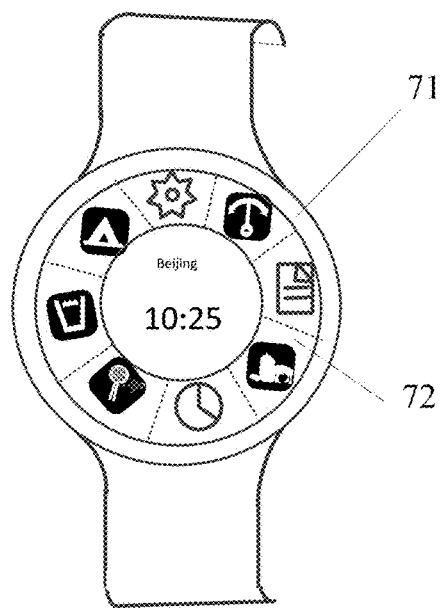
FIG. 11B is a schematic diagram of rotating the second graphical interface by a move operation in the second embodiment.

For example, with reference to FIG. 11A, number 71 represents the second sub sensing section, i.e., the annular sensing area, number 72 represents the second graphical interface, number 73 represents the first sub-operational track of the track of move operation, and number 74 represents the second sub-operational track of the track of move operation. As shown in the drawings, the first sub-operational track and the second sub-operational track are not in a same line, and the first sub-operational track and the second sub-operational track are all positioned on the annular sensing area, and a distance between these two tracks is larger than maximum diameter of the annular sensing area, that is, the move operation is an operation for rotating the second graphical interface. After the move operation is executed by the user, with reference to FIG. 11B, number 71 represents the annular sensing area, number 72 represents the second graphical interface, as compared with FIG. 11A, it can be known that the second graphical interface is rotated clockwise.

Wherein, determining the first operational direction as the rotation direction of the second graphical interface when the first operational direction is consistent with the second operational direction and controlling the second graphical interface to rotate according to the rotation direction may be specifically: determining the first operational direction as the rotation direction of the second graphical interface when the first operational direction is consistent with the second operational direction; determining a first angle formed by a first start point and a first end point of the first sub-operational track with the center of circle and determining a second angle formed by a second start point and a second end point of second first sub-operational track with the center of circle according to the track of move operation; determining an angle of rotation of the second graphical interface according to the first angle and the second angle; and controlling the second graphical interface to rotate according to the angle of rotation and the rotation direction.

That is, in the second embodiment, when the first sub-operational track and the second sub-operational track of the track of move operation are not in a same line, it can determine that the move operation is an operation for controlling the second graphical interface to rotate, and it in turn decides whether the first operational direction and the second operational direction are consistent, for example, whether they are both clockwise or counterclockwise. And, when the two directions are consistent, the first operational direction or the second operational direction therein may be determined as the direction when the second display interface rotates.

At the same time, in practical operating procedure, the first angle between the first sub-operational track and the center of circle and the second angle between the second sub-operational track and the center of circle may also be determined according to the track of move operation, and the first angle and the second angle may be different. For example, the user moves his thumb and forefinger at two relative positions in the annular sensing area clockwise, due to flexibility of the forefinger, a corresponding first track of movement when the forefinger moves may be longer than a corresponding second track of movement when the thumbnail moves, then, the first angle determined through the track of movement would be larger than the second angle.

In the second embodiment, determining the angle of rotation of the second graphical interface according to the first angle and the second angle may be specifically: determining an angle between the first angle and the second angle as the angle of rotation. For example, the first angle and the second angle constitute a range of angle, and the angle of rotation may be any one angle in the range of angle. Or a larger angle of the first angle and the second angle may be determined as the angle of rotation, or a smaller angle of the first angle and the second angle may be determined as the angle of rotation, or an angle difference between the first angle and the second angle may be determined as the angle of rotation, and so on, so that it is able to control the rotation of the second graphical interface relatively flexibly.

For example, the determined rotation direction is clockwise, and the first angle determined according to the first sub-operational track is 60°, the second angle determined according to the second sub-operational track is 40°. At this time, if an angle between the first angle and the second angle is determined as the angle of rotation, then the determined angle of rotation may be 50°, the second graphical interface would rotate by 50° clockwise according to the rotation direction; if a larger one of the first angle and the second angle is determined as the angle of rotation, then the determined angle of rotation is 60°, the second graphical interface would rotate by 60° clockwise according to the rotation direction.

In the second embodiment, when the move operation is determined as an operation for controlling the second graphical interface to rotate, the direction and the angle of the rotation of the second graphical interface can be determined according to the track of move operation generated thereby, so as to control the second graphic rotate correspondingly, thus, the rotation of the second graphical interface can be controlled through the annular sensing area in the procedure in which the user views the circular screen, so that the user can view other parts of the display interface better. For example, the current second graphical interface is in a magnified status, and only two second identification objects are displayed in the circular screen, at this time, the user can control the second graphical interface to rotate by the above-described operation, so as to see other second identification objects.

It needs to explain that in the above-described three kinds of adjusting methods, it is not only limited to the adjustment to the second graphical interface in the circular screen, it may also be adjustment to interface of an application displayed in the circular screen corresponding to a certain second identification object, for example, magnification, reduction or rotation or the like to the interface of the map application.

In the second embodiment, when the electronic apparatus displays the first graphical interface and run the N functional modules, the user may make the electronic apparatus to obtain the first manipulation instruction to display the second graphical interface through the operation carried out on the sensing section of the input unit, so as to control the electronic apparatus to run the functional module corresponding to the P second identification objects. However, in a usual case of displaying only the first graphical interface, redundant functional modules do not need to be run, so that the power consumption of the electronic apparatus is reduced. And, since the sensing section of the input unit can be positioned at any position on the frame structure body other than the display screen, the electronic apparatus is able to provide larger operational region to the user, so that the electronic apparatus can obtain corresponding operation instruction and make corresponding response, for example, displaying the second graphical interface or invoking the application corresponding to the second identification object when the user operates on other regions than the display screen, without operating in the display screen with limited size. Therefore, by using the input unit positioned at other part in the frame structure body than the display screen to input, the conventional limitation of operational region of the electronic apparatus with less size can be improved, and erroneous response of the electronic apparatus is reduced, and the display screen is made not to be blocked in the operational process, so as to improve display effect of display screen and the user's experience.

Figure 12:
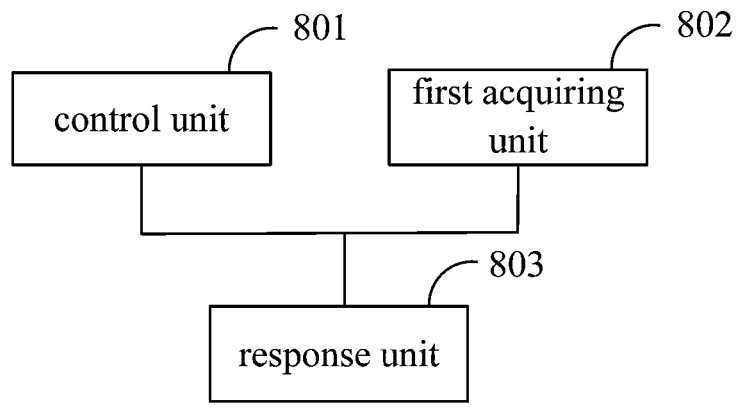
FIG. 12 is a schematic diagram of primary structure of the electronic apparatus in the second embodiment.

With reference to FIG. 12, based on a same inventive concept, the second embodiment further provides an electronic apparatus including: a frame structure body including a fixing structure which is able to fix the electronic apparatus on a first operation body; a display unit fixed on the frame structure body and including a display screen; an input unit fixed by the frame structure body and of which a sensing section is able to be positioned at any position on the frame structure body other than the display screen; and a processor connected with the input unit and fixed by the frame structure body and for controlling the electronic apparatus according to parameter obtained by the sensing section of the input unit; and the electronic apparatus may include a control unit 801, a first acquiring unit 802 and a response unit 803.

The control unit 801 may be for controlling the electronic apparatus to display a first graphical interface including M first identification objects which are able to feedback working parameters of N functional modules corresponding to the M first identification objects of the electronic apparatus in real time when the electronic apparatus is fixed on the first operation body by the fixing structure, here, M and N being positive integers.

The first acquiring unit 802 may be for obtaining a first manipulation instruction.

The response unit 803 may be for controlling the electronic apparatus to display the second graphical interface in response to the first manipulation instruction, the second graphical interface includes the P second identification objects which are for identifying application entry which is able to invoke applications corresponding to the P second identification objects, here P is a positive integer; wherein, when a trigger operation with respect to an application entry corresponding to the i-th second identification object in the P second identification objects is obtained, an application corresponding to the i-th second identification object is invoked, here, i is a positive integer that is not larger than P.

Figure 13:
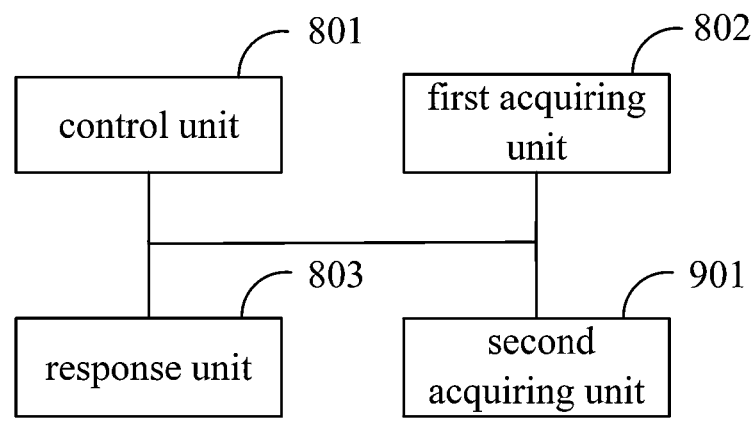
FIG. 13 is a schematic diagram one of the structure of the electronic apparatus in the second embodiment.

Preferably, in the second embodiment, the electronic apparatus further includes a second acquiring unit 901, with reference to FIG. 13.

The second acquiring unit 901 may be for obtaining a trigger operation with respect to an application entry corresponding to the i-th second identification object in the P second identification objects and invoking an application corresponding to the i-th second identification object.

In the second embodiment, the display screen is a circular screen, and the frame structure body includes a frame main body having a shape matched with the circular screen and for fixing the circular screen, and the second graphical interface is an annular interface, and a first sensing sub-section in the sensing section is provided at a locked structure of the fixing structure, and the first sensing sub-section is a circular sensing section. When the electronic apparatus is fixed on the first operation body by fixing structure, the circular screen is positioned at a first surface of the first operation body, and the circular sensing section is positioned at a second surface of the first operation body, and the first surface is opposite to the second surface and the circular screen is opposite to the circular sensing section.

Figure 14:
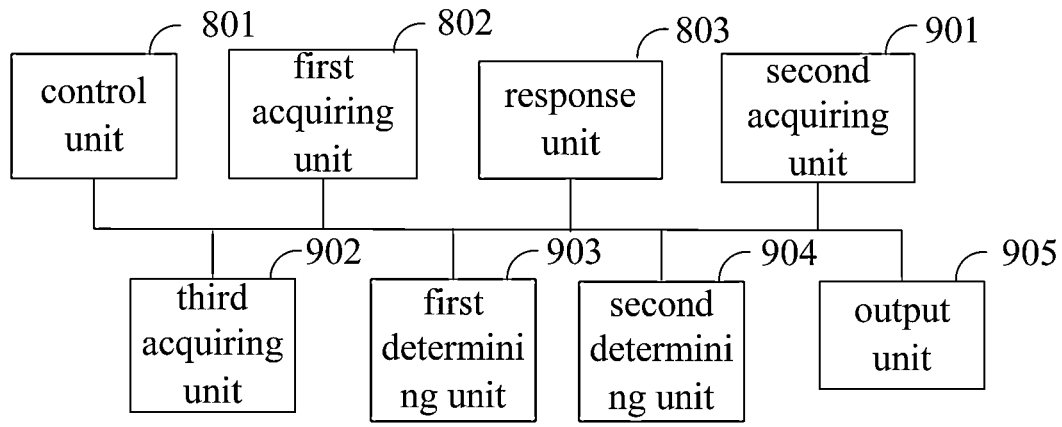
FIG. 14 is a schematic diagram two of the structure of the electronic apparatus in the second embodiment.

The electronic apparatus further includes a third acquiring unit 902, a first determining unit 903, a second determining unit 904 and an output unit 905, with reference to FIG. 14.

The third acquiring unit 902 may be for obtaining a track of move operation generated by a move operation carried out on the circular sensing section by the second operation body through the circular sensing section.

The first determining unit 903 may be for determining a first position corresponding to the move operation on the circular sensing section according to the track of move operation.

The second determining unit 904 may be for determining the second identification object corresponding to the first position according to correspondence relationship between position on the circular sensing section and the second identification object.

The output unit 905 may be for controlling to output prompt information at identification region in the second graphical interface where the determined second identification object is.

In the second embodiment, the display screen is a circular screen, and the frame structure body includes a frame main body having a shape matched with the circular screen and for fixing the circular screen, and the second graphical interface is an annular interface, and a sensing section of the input unit is provided on the part of the frame main body, and a second sub-sensing section included in sensing section is at a periphery region adjacent to the display screen and the second sub sensing section is an annular sensing area and shares one center of circle with the display screen.

Figure 15:
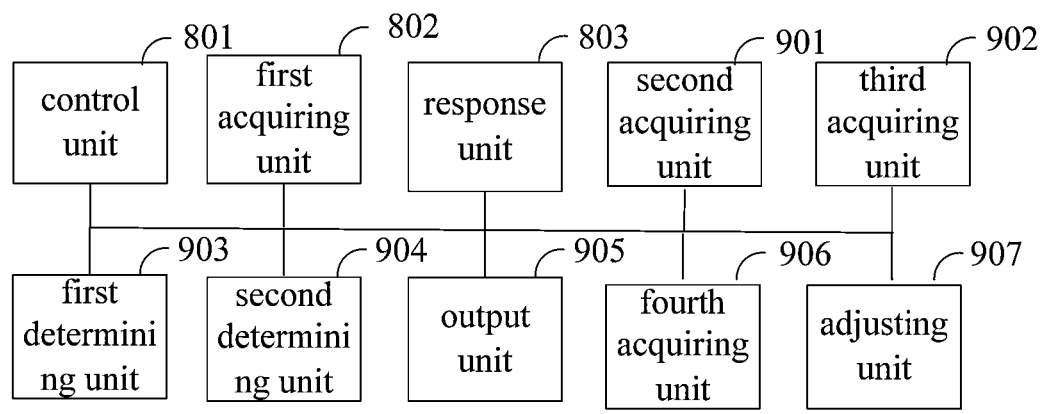
FIG. 15 is a schematic diagram three of the structure of the electronic apparatus in the second embodiment.

The electronic apparatus further includes a fourth acquiring unit 906 and an adjusting unit 907, with reference to FIG. 15.

The fourth acquiring unit 907 may be for obtaining a track of move operation generated by a move operation carried out by the second operation body in the annular sensing area through the annular sensing area.

The adjusting unit 907 may be for adjusting display modes of the second graphical interface according to the track of move operation.

In the second embodiment, the adjusting unit 907 is specifically for: magnifying the second graphical interface in a first preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track increases gradually.

Preferably, in the second embodiment, the adjusting unit 907 may be specifically for: reducing the second graphical interface in a second preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track decreases gradually.

Preferably, in the second embodiment, the adjusting unit 907 may be specifically for: controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

Preferably, in the second embodiment, the adjusting unit 907 being specifically for controlling the second graphical interface to rotate according to the first sub-operational track and the second sub-operational track may be specifically: deciding whether a first operational direction corresponding to the first sub-operational track is consistent with a second operational direction corresponding to the second sub-operational track; determining the first operational direction as rotation direction of the second graphical interface when the first operational direction is consistent with the second operational direction and controlling the second graphical interface to rotate according to the rotation direction.

Preferably, in the second embodiment, the adjusting module 907 being specifically for determining the first operational direction as the rotation direction of the second graphical interface when the first operational direction is consistent with the second operational direction and controlling the second graphical interface to rotate according to the rotation direction may be specifically: determining the first operational direction as the rotation direction of the second graphical interface when the first operational direction is consistent with the second operational direction; determining a first angle formed by a first start point and a first end point of the first sub-operational track with the center of circle and determining a second angle formed by a second start point and a second end point of second first sub-operational track with the center of circle according to the track of move operation; determining an angle of rotation of the second graphical interface according to the first angle and the second angle; and controlling the second graphical interface to rotate according to the angle of rotation and the rotation direction.

The second embodiment provides an information processing method applied in an electronic apparatus, the electronic apparatus includes: a frame structure body including a fixing structure which is able to fix the electronic apparatus on a first operation body; a display unit fixed on the frame structure body and including a display screen; an input unit fixed by the frame structure body and of which a sensing section is able to be positioned at any position on the frame structure body other than the display screen; and a processor connected with the input unit and fixed by the frame structure body and for controlling the electronic apparatus according to parameter obtained by the sensing section of the input unit;

The method includes: controlling the electronic apparatus to display a first graphical interface including M first identification objects which are able to feedback working parameters of N functional modules corresponding to the M first identification objects of the electronic apparatus in real time when the electronic apparatus is fixed on the first operation body by the fixing structure, here, M and N being positive integers; obtaining a first manipulation instruction; and controlling the electronic apparatus to display a second graphical interface including P second identification objects for identifying application entries which are able to invoke applications corresponding to the P second identification objects in response to the first manipulation instruction, here, P being a positive integer; wherein, when a trigger operation with respect to an application entry corresponding to the i-th second identification object in the P second identification objects is obtained, an application corresponding to the i-th second identification object is invoked, here, i is a positive integer that is not larger than P.

In the second embodiment, since both of the display unit and the input unit are fixed on the frame structure body, when the electronic apparatus is fixed on the first operation body and display the first graphical interface by the display unit, the user can know current parameter status of the electronic apparatus conveniently through working parameter of N functional modules corresponding thereto feedback by the M first identification objects, for example, electric power, time, signal or the like. That is, when the electronic apparatus displays the M first identification objects, only operational modules corresponding to the M first identification objects needs to run, so the electronic apparatus can be in a status of low power consumption. And, when the first operational instruction is obtained, the electronic apparatus is controlled to include the second graphical interface including the P second identification objects, and at this time, the electronic apparatus only needs to run the functional modules corresponding to the P second identification objects without running the N functional modules corresponding to the M first identification objects any longer. Thus, when the electronic apparatus switches between the first graphical interface and the second graphical interface, only the functional modules corresponding to the identification objects in the current graphical interface needs to be run, so that the power consumption of the electronic apparatus is reduced and usage time of the electronic apparatus is extended.

Here, those skilled in the art can understand, in order to reduce the power consumption of the wearable electronic apparatus, the technical solution according to the first embodiment and the technical solution according to a second embodiment can be used separately, or can be used in combination with each other.

And, the technical solution the first embodiment and the technical solution the second embodiment may refer to a same wearable electronic apparatus, or may refer to different wearable electronic apparatus. At the time of referring to the same wearable electronic apparatus, those skilled in the art can understand correspondence relationship of the respective components. For example, the body unit in the wearable electronic apparatus according to the first embodiment corresponds to the frame main body in the wearable electronic apparatus according to a second embodiment, and the fixing unit in the wearable electronic apparatus according to the first embodiment corresponds to the fixing structure in the wearable electronic apparatus according to a second embodiment. Those skilled in the art can understand it clearly based on the above description of the specification, thus it is no longer described here.

Further, the respective functional modules in the technical solution of the first embodiment and the technical solution of the second embodiment may be corresponding to each other. For example, the first processing unit or the second processing unit in the wearable electronic apparatus according to the first embodiment may execute functions of the control unit and the response unit in the wearable electronic apparatus according to a second embodiment.

In particular, in the technical solution according to a second embodiment, when the electronic apparatus is controlled to display the first graphical interface including the M first identification objects, the electronic apparatus can be regarded as being in a first mode, and when the electronic apparatus is controlled to display the second graphical interface including the P second identification objects, the electronic apparatus can be regarded as being in a second mode. And, those skilled in the art can understand, since the M first identification objects feedback working parameter of the N functional modules corresponding to the M first identification objects of the electronic apparatus in real time in the first mode, the power consumption of the electronic apparatus in the first mode may be regarded as lower.

Thus, in case that the electronic apparatus according to the embodiments includes the first processing unit and the second processing unit as in the first embodiment and the average power consumption of the second processing unit is less than the average power consumption of the first processing unit, the second processing unit is regarded as executing the processing of controlling the electronic apparatus to display the first graphical interface including the M first identification objects, and the first processing unit is regarded as executing the processing of controlling the electronic apparatus to display the second graphical interface including the P second identification objects.

However, if in the technical solution according to a second embodiment, the number of the P second identification objects displayed when the electronic apparatus is controlled to display the second graphical interface including the P second identification objects, i.e., in the second mode is relatively small, the power consumption of the electronic apparatus in the second mode may be relatively small.

Therefore, similarly, in case that the electronic apparatus according to the embodiments includes the second processing unit and the second processing unit as in the first embodiment and the average power consumption of the second processing unit is less than the average power consumption of the second processing unit, the first processing unit is regarded as executing the processing of controlling the electronic apparatus to display the first graphical interface including the M first identification objects, and the second processing unit is regarded as executing the processing of controlling the electronic apparatus to display the second graphical interface including the P second identification objects.

For the other details, those skilled in the art can understand clearly based on description of the specification, and it is no longer described here.

Therefore, when the technical solution according to the first embodiment is applied separately, the electronic apparatus and the information processing method according to the embodiments may be configured as follows:

(1) An electronic apparatus including:

A first processing unit for executing an operation of a first type;

A second processing unit for executing an operation of a second type, here, average power consumption of the second processing unit is less than the average power consumption of the first processing unit;

A sharing unit connected to the first processing unit and the second processing unit and for operating cooperatively selectively with either or both of the first processing unit and the second processing unit according to predetermined condition; and A fixing unit for fixing relative position relation of the electronic apparatus with the user.

(2) The electronic apparatus according to according to (1), further includes:

A body unit including at least the first processing unit and the second processing unit;

Wherein, the fixing unit is connected to the body unit and the fixing unit includes at least a fixing status in which the fixing unit is able to be as an annular space or at least a part of an approximate annular space satisfying a first predetermined condition, here, the annular space or the approximate annular space is able to surround at periphery of a columnar body satisfying a second predetermined condition.

(3) The electronic apparatus according to (1), wherein the electronic apparatus includes the first processing subsystem including at least the sharing unit and the first processing unit and the second processing subsystem including at least the sharing unit and the second processing unit, average power consumption of the second processing subsystem is less than the average power consumption of the first processing subsystem.

(4) The electronic apparatus according to (3), wherein the sharing unit includes a display unit connected to the first processing unit and the second processing unit so as to display content output from the first processing unit or the second processing unit selectively according to control of the first processing unit and/or the second processing unit.

(5) The electronic apparatus according to (3), wherein the first processing subsystem further include a first display connected to the first processing unit and for displaying content outputted from the first processing unit according to the control of the first processing unit, and the second processing subsystem may further include a second display connected to the second processing unit and for displaying content outputted from the second processing unit according to the control of the second processing unit, and average power consumption of the first display is larger than the average power consumption of the second display.

(6) The electronic apparatus according to (3), wherein the second display is further connected to the first processing unit, so that the second display displays content outputted from the first processing unit according to the control of the first processing unit; or The second processing unit is further connected to the first processing unit, so that the second processing unit receives content output from the first processing unit and control the second display to display the content received from the first processing unit when processing of the first processing unit is completed.

(7) The electronic apparatus according to (5), wherein the first display and the second display are provided overlapped in radial direction of the annular space, and when the first display or the second display provided at inner side of the radial direction of the annular space displays, it is controlled so that light transmittance of the second display or the first display provided at outer side of the radial direction of the annular space is larger than a predetermined threshold.

(8) The electronic apparatus according to (3) wherein the sharing unit further includes a power supple unit for providing electric power to the respective units of the electronic apparatus and configured to provide the electric power only to the second processing subsystem when a first predetermined condition is satisfied.

(9) The electronic apparatus according to (8), wherein the power supple unit is provided in the fixing unit.

(10) The electronic apparatus according to (3), wherein the sharing unit includes a communication unit connected to the first processing unit and the second processing unit and for connecting to network according to control of the first processing unit or the second processing unit according to a predetermined condition.

(11) The electronic apparatus according to (3), wherein the first processing subsystem includes the first communication unit and the second processing subsystem includes the second communication unit, the first communication unit is connected to the first processing unit and connected to the network according to the control of the first processing unit, the second communication unit is connected to the second processing unit and is connected to the network according to the control of the second processing unit, communication distance of the first communication unit is larger than or equal to a predetermined threshold, and communication distance of the second communication unit is less than a predetermined threshold, here, power consumption of the first communication unit is larger than that of the second communication unit; the first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

(12) The electronic apparatus according to (3), wherein the first processing subsystem includes the first communication unit and the second communication unit which are connected to the first processing unit and connected to the network according to the control of the first processing unit, the communication distance of the first communication unit is larger than or equal to a predetermined threshold, and the communication distance of the second communication unit is less than the predetermined threshold, here, the power consumption of the first communication unit is larger than that of the second communication unit; the first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

(13) An information processing method applied in an electronic apparatus including a fixing unit for fixing relative position relation of the electronic apparatus with the user, the information processing method includes: executing an operation of a first type by a first processing unit of the electronic apparatus; executing an operation of a second type by a second processing unit of the electronic apparatus, where average power consumption of the second processing unit is less than average power consumption of the first processing unit; and operating cooperatively with either or both of the first processing unit and the second processing unit selectively by a sharing unit of the electronic apparatus according to predetermined conditions, wherein, the sharing unit is connected to the first processing unit and the second processing unit.

Further, when the technical solution according to the first embodiment and the technical solution according to a second embodiment are applied in combination with each other, the electronic apparatus according to the embodiments can be configured as follows:

(14) The electronic apparatus according to any one of (1) to (12), further includes: a frame structure body, a display unit and an input unit, wherein, the frame structure body includes the fixing unit which is able to fix the electronic apparatus on a first operation body of a user; a first acquiring unit for obtaining a first manipulation instruction; the display unit is fixed on the frame structure body and includes a display screen; the input unit is fixed through the frame structure body and a sensing section of input unit is able to be positioned at any position on the frame structure body other than the display screen; the first processing unit and the second processing unit are connected to the input unit and are fixed through the frame structure body and control the electronic apparatus according to parameter obtained by the sensing section of the input unit;

Wherein, the second processing unit is configured to control the electronic apparatus to display a first graphical interface including M first identification objects which is able to feedback working parameter of N functional modules of the electronic apparatus corresponding to the M first identification objects when the electronic apparatus is fixed on the first operation body by the fixing unit, here, M and N are positive integers;

The first processing unit is configured to control the electronic apparatus to display a second graphical interface including P second identification objects for identifying application entries which are able to invoke applications corresponding to the P second identification objects in response to the first manipulation instruction, here, P is a positive integer;

Wherein, when a trigger operation with respect to an application entry corresponding to the i-th second identification object in the P second identification objects is obtained, an application corresponding to the i-th second identification object is invoked, here, i is a positive integer that is not larger than P.

(15) The electronic apparatus according to (14), wherein the electronic apparatus further includes a second acquiring unit for obtaining a trigger operation with respect to an application entry corresponding to the i-th second identification object in the P second identification objects and invoking an application corresponding to the i-th second identification object.

(16) The electronic apparatus according to (15), wherein the display screen is a circular screen, and the frame structure body includes a frame main body having a shape matched with the circular screen and for fixing the circular screen, the second graphical interface is an annular interface, a first sensing sub-section in the sensing section is provided at a locked structure of the fixing structure, and the first sensing sub-section is a circular sensing section, when the electronic apparatus is fixed on the first operation body by fixing structure, the circular screen is positioned at a first surface of the first operation body, the circular sensing section is positioned at a second surface of the first operation body, the first surface is opposite to the second surface and the circular screen is opposite to the circular sensing section; the electronic apparatus further includes:

A third acquiring unit for obtaining a track of move operation generated by a move operation carried out on the circular sensing section by the second operation body through the circular sensing section;

A first determining unit for determining a first position corresponding to the move operation on the circular sensing section according to the track of move operation;

A second determining unit for determining the second identification object corresponding to the first position according to correspondence relationship between position on the circular sensing section and the second identification object; and An output unit for controlling to output prompt information at identification region in the second graphical interface where the determined second identification object is.

(17) The electronic apparatus according to any one of (14) to (16), wherein the display screen is a circular screen, the frame structure body includes a frame main body having a shape matched with the circular screen and for fixing the circular screen, the second graphical interface is an annular interface, a sensing section of the input unit is provided on the part of the frame main body, and a second sub-sensing section included in sensing section is at a periphery region adjacent to the display screen and the second sub sensing section is an annular sensing area and shares one center of circle with the display screen; the electronic apparatus further includes:

A fourth acquiring unit for obtaining a track of move operation generated by a move operation carried out by the second operation body in the annular sensing area through the annular sensing area; and An adjusting unit for adjusting the display modes of the second graphical interface according to the track of move operation.

(18) The electronic apparatus according to (17), wherein the adjusting unit is specifically for: magnifying the second graphical interface in a first preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track increases gradually.

(19) The electronic apparatus according to (17), wherein the adjusting unit is specifically for: reducing the second graphical interface in a second preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track decreases gradually.

(20) The electronic apparatus according to (17), wherein the adjusting unit is specifically for: controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

(21) The electronic apparatus according to (20), wherein the adjusting unit being specifically for controlling the second graphical interface to rotate according to the first sub-operational track and the second sub-operational track is specifically: deciding whether a first operational direction corresponding to the first sub-operational track is consistent with a second operational direction corresponding to the second sub-operational track; determining the first operational direction as rotation direction of the second graphical interface when the first operational direction is consistent with the second operational direction and controlling the second graphical interface to rotate according to the rotation direction.

(22) The electronic apparatus according to (21), wherein the adjusting module being specifically for determining the first operational direction as rotation direction of the second graphical interface when the first operational direction is consistent with the second operational direction and controlling the second graphical interface to rotate according to the rotation direction is specifically: determining the first operational direction as the rotation direction of the second graphical interface when the first operational direction is consistent with the second operational direction; determining a first angle formed by a first start point and a first end point of the first sub-operational track with the center of circle and determining a second angle formed by a second start point and a second end point of second first sub-operational track with the center of circle according to the track of move operation; determining an angle of rotation of the second graphical interface according to the first angle and the second angle; and controlling the second graphical interface to rotate according to the angle of rotation and the rotation direction

(23) the information processing method according to (13), the electronic apparatus includes: a frame structure body, a display unit and an input unit, wherein, the frame structure body includes the fixing unit which is able to fix information processing method on a first operation body of a user; the display unit is fixed on the frame structure body and includes a display screen; the input unit is fixed through the frame structure body and a sensing section of input unit is able to be positioned at any position on the frame structure body other than the display screen; and the first processing unit and the second processing unit are connected to the input unit and are fixed through the frame structure body and control the electronic apparatus according to parameter obtained by the sensing section of the input unit;

The information processing method includes:

Wherein, executing the operation of the second type by the second processing unit is specifically: controlling the electronic apparatus to display a first graphical interface including M first identification objects which are able to feedback working parameter of N functional modules corresponding to the M first identification objects of the electronic apparatus in real time by the second processing unit when the electronic apparatus is fixed on the first operation body by the fixing structure, here, M and N being positive integers; obtaining a first manipulation instruction;

Executing the operation of the first type by the first processing unit is specifically: controlling the electronic apparatus to display a second graphical interface including P second identification objects for identifying application entries which are able to invoke applications corresponding to the P second identification objects by the first processing unit in response to the first processing unit here, P is a positive integer; wherein, when a trigger operation with respect to an application entry corresponding to the i-th second identification object in the P second identification objects is obtained, an application corresponding to the i-th second identification object is invoked, here, i is a positive integer that is not larger than P.

(24) The method according to (23), wherein after controlling the electronic apparatus to display the second graphical interface in response to the first manipulation instruction, the method further includes: obtaining the trigger operation with respect to the application entry corresponding to the i-th second identification object in the P second identification objects and invoking the application corresponding to the i-th second identification object.

(25) The method according to (22), wherein the display screen is a circular screen, and the frame structure body includes a frame main body having a shape matched with the circular screen and for fixing the circular screen, and the second graphical interface is an annular interface, and a first sensing sub-section in the sensing section is provided at a locked structure of the fixing structure, and the first sensing sub-section is a circular sensing section, when the electronic apparatus is fixed on the first operation body by fixing structure, the circular screen is positioned at a first surface of the first operation body, and the circular sensing section is positioned at a second surface of the first operation body, and the first surface is opposite to the second surface and the circular screen is opposite to the circular sensing section; after controlling the electronic apparatus to display the second graphical interface in response to the first manipulation instruction, the method further includes:

Obtaining a track of move operation generated by a move operation carried out on the circular sensing section by the second operation body through the circular sensing section; determining a first position corresponding to the move operation on the circular sensing section according to the track of move operation; determining the second identification object corresponding to the first position according to correspondence relationship between position on the circular sensing section and the second identification object; and controlling to output prompt information at identification region in the second graphical interface where the determined second identification object is.

(26) The method according to any one of (23) to (25), wherein the display screen is a circular screen, and the frame structure body includes a frame main body having a shape matched with the circular screen and for fixing the circular screen, and the second graphical interface is an annular interface, and a sensing section of the input unit is provided on the part of the frame main body, and a second sub-sensing section included in sensing section is at a periphery region adjacent to the display screen and the second sub sensing section is an annular sensing area and shares one center of circle with the display screen; after controlling the electronic apparatus to display the second graphical interface in response to the first manipulation instruction, the method further includes: obtaining a track of move operation generated by a move operation carried out by the second operation body in the annular sensing area through the annular sensing area; and adjusting display modes of the second graphical interface according to the track of move operation.

(29) The method according to (26), wherein adjusting display modes of the second graphical interface according to track of move operation is specifically: magnifying the second graphical interface in a first preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track increases gradually.

(29) The method according to (26), wherein adjusting display modes of the second graphical interface according to track of move operation is specifically: reducing the second graphical interface in a second preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track decreases gradually.

(29) The method according to (26), wherein adjusting display modes of the second graphical interface according to track of move operation is specifically: controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

(30) The method according to (29), wherein controlling the second graphical interface to rotate according to the first sub-operational track and the second sub-operational track is specifically: deciding whether a first operational direction corresponding to the first sub-operational track is consistent with a second operational direction corresponding to the second sub-operational track; and determining the first operational direction as rotation direction of the second graphical interface when the first operational direction is consistent with the second operational direction and controlling the second graphical interface to rotate according to the rotation direction.

(31) The method according to (30), wherein determining the first operational direction as rotation direction of the second graphical interface when the first operational direction is consistent with the second operational direction and controlling the second graphical interface to rotate according to the rotation direction is specifically: determining the first operational direction as the rotation direction of the second graphical interface when the first operational direction is consistent with the second operational direction; determining a first angle formed by a first start point and a first end point of the first sub-operational track with the center of circle and determining a second angle formed by a second start point and a second end point of second first sub-operational track with the center of circle according to the track of move operation; determining an angle of rotation of the second graphical interface according to the first angle and the second angle; and controlling the second graphical interface to rotate according to the angle of rotation and the rotation direction.

When the technical solution according to a second embodiment is applied separately, the information processing method and the electronic apparatus according to the embodiments can be configured as follows:

(32) An information processing method applied in an electronic apparatus including a frame structure body, a display unit, an input unit and a processor; the frame structure body including a fixing structure which is able to fix the electronic apparatus on a first operation body; the display unit being fixed on the frame structure body and including a display screen; an input unit being fixed by the frame structure body and of which a sensing section is able to be positioned at any position on the frame structure body other than the display screen; and the processor being connected with the input unit and fixed by the frame structure body and for controlling the electronic apparatus according to parameter obtained by the sensing section of the input unit;

The method includes: controlling the electronic apparatus to display a first graphical interface including M first identification objects which are able to feedback working parameter of N functional modules corresponding to the M first identification objects of the electronic apparatus in real time when the electronic apparatus is fixed on the first operation body by the fixing structure, here, M and N being positive integers; obtaining a first manipulation instruction; and controlling the electronic apparatus to display a second graphical interface including P second identification objects for identifying application entries which are able to invoke applications corresponding to the P second identification objects in response to the first manipulation instruction, here, P being a positive integer; wherein, when a trigger operation with respect to an application entry corresponding to the i-th second identification object in the P second identification objects is obtained, an application corresponding to the i-th second identification object is invoked, here, i is a positive integer that is not larger than P.

(33) The method according to (32), wherein after controlling the electronic apparatus to display the second graphical interface in response to the first manipulation instruction, the method further includes: obtaining the trigger operation with respect to the application entry corresponding to the i-th second identification object in the P second identification objects and invoking the application corresponding to the i-th second identification object.

(34) The method according to (33), wherein the display screen is a circular screen, and the frame structure body includes a frame main body having a shape matched with the circular screen and for fixing the circular screen, the second graphical interface is an annular interface, a first sensing sub-section in the sensing section is provided at a locked structure of the fixing structure, and the first sensing sub-section is a circular sensing section, when the electronic apparatus is fixed on the first operation body by fixing structure, the circular screen is positioned at a first surface of the first operation body, the circular sensing section is positioned at a second surface of the first operation body, the first surface is opposite to the second surface and the circular screen is opposite to the circular sensing section;

After controlling the electronic apparatus to display the second graphical interface in response to the first manipulation instruction, the method further includes: obtaining a track of move operation generated by a move operation carried out on the circular sensing section by the second operation body through the circular sensing section; determining a first position corresponding to the move operation on the circular sensing section according to the track of move operation; determining the second identification object corresponding to the first position according to correspondence relationship between position on the circular sensing section and the second identification object; and controlling to output prompt information at identification region in the second graphical interface where the determined second identification object is.

(35) The method according to any one of (32) to (34), wherein the display screen is a circular screen, the frame structure body includes a frame main body having a shape matched with the circular screen and for fixing the circular screen, the second graphical interface is an annular interface, a sensing section of the input unit is provided on the part of the frame main body, and a second sub-sensing section included in sensing section is at a periphery region adjacent to the display screen and the second sub sensing section is an annular sensing area and shares one center of circle with the display screen; after controlling the electronic apparatus to display the second graphical interface in response to the first manipulation instruction;

The method further includes: obtaining a track of move operation generated by a move operation carried out by the second operation body in the annular sensing area through the annular sensing area; and adjusting display modes of the second graphical interface according to the track of move operation.

(36) The method according to (35), wherein adjusting display modes of the second graphical interface according to track of move operation is specifically: magnifying the second graphical interface in a first preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track increases gradually.

(37) The method according to (35), wherein adjusting display modes of the second graphical interface according to track of move operation is specifically: reducing the second graphical interface in a second preset proportion according to the first sub-operational track and the second sub-operational track if it determines that the track of move operation includes the first sub-operational track and the second sub-operational track; and wherein, if the first sub-operational track and the second sub-operational track are opposite in direction, distance between the first sub-operational track and the second sub-operational track decreases gradually.

(38) The method according to (35), wherein adjusting display modes of the second graphical interface according to track of move operation is specifically: controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

(39) The method according to (38), wherein controlling the second graphical interface to rotate according to the first sub-operational track and the second sub-operational track is specifically: deciding whether a first operational direction corresponding to the first sub-operational track is consistent with a second operational direction corresponding to the second sub-operational track; and determining the first operational direction as rotation direction of the second graphical interface when the first operational direction is consistent with the second operational direction and controlling the second graphical interface to rotate according to the rotation direction.

(40) The method according to (39), wherein determining the first operational direction as rotation direction of the second graphical interface when the first operational direction is consistent with the second operational direction and controlling the second graphical interface to rotate according to the rotation direction is specifically: determining the first operational direction as the rotation direction of the second graphical interface when the first operational direction is consistent with the second operational direction; determining a first angle formed by a first start point and a first end point of the first sub-operational track with the center of circle and determining a second angle formed by a second start point and a second end point of second first sub-operational track with the center of circle according to the track of move operation; determining an angle of rotation of the second graphical interface according to the first angle and the second angle; and controlling the second graphical interface to rotate according to the angle of rotation and the rotation direction.

(41) An electronic apparatus including: a frame structure body, a display unit, an input unit and a processor, wherein the frame structure body including a fixing structure which is able to fix the electronic apparatus on a first operation body; the display unit being fixed on the frame structure body and including a display screen; an input unit being fixed by the frame structure body and of which a sensing section is able to be positioned at any position on the frame structure body other than the display screen; and the processor being connected with the input unit and fixed by the frame structure body and for controlling the electronic apparatus according to parameter obtained by the sensing section of the input unit;

The electronic apparatus includes: a control unit for controlling the electronic apparatus to display a first graphical interface including M first identification objects which are able to feedback working parameter of N functional modules corresponding to the M first identification objects of the electronic apparatus in real time when the electronic apparatus is fixed on the first operation body by the fixing structure, here, M and N being positive integers; a first acquiring unit for obtaining a first manipulation instruction; and a response unit for controlling the electronic apparatus to display a second graphical interface including P second identification objects for identifying application entries which are able to invoke applications corresponding to the P second identification objects in response to the first manipulation instruction, here, P is a positive integer; wherein, when a trigger operation with respect to an application entry corresponding to the i-th second identification object in the P second identification objects is obtained, an application corresponding to the i-th second identification object is invoked, here, i is a positive integer that is not larger than P.

(42) The electronic apparatus according to (41), wherein the electronic apparatus further includes a second acquiring unit for obtaining a trigger operation with respect to an application entry corresponding to the i-th second identification object in the P second identification objects and invoking an application corresponding to the i-th second identification object.

(43) The electronic apparatus according to (42), wherein the display screen is a circular screen, and the frame structure body includes a frame main body having a shape matched with the circular screen and for fixing the circular screen, the second graphical interface is an annular interface, a first sensing sub-section in the sensing section is provided at a locked structure of the fixing structure, and the first sensing sub-section is a circular sensing section, when the electronic apparatus is fixed on the first operation body by fixing structure, the circular screen is positioned at a first surface of the first operation body, the circular sensing section is positioned at a second surface of the first operation body, the first surface is opposite to the second surface and the circular screen is opposite to the circular sensing section;

The electronic apparatus further includes: a third acquiring unit for obtaining a track of move operation generated by a move operation carried out on the circular sensing section by the second operation body through the circular sensing section; a first determining unit for determining a first position corresponding to the move operation on the circular sensing section according to the track of move operation; a second determining unit for determining the second identification object corresponding to the first position according to correspondence relationship between position on the circular sensing section and the second identification object; and an output unit for controlling to output prompt information at identification region in the second graphical interface where the determined second identification object is.

(44) The electronic apparatus according to any one of (41) to (43), wherein the display screen is a circular screen, the frame structure body includes a frame main body having a shape matched with the circular screen and for fixing the circular screen, the second graphical interface is an annular interface, a sensing section of the input unit is provided on the part of the frame main body, and a second sub-sensing section included in sensing section is at a periphery region adjacent to the display screen and the second sub sensing section is an annular sensing area and shares one center of circle with the display screen;

The electronic apparatus further includes: a fourth acquiring unit for obtaining a track of move operation generated by a move operation carried out by the second operation body in the annular sensing area through the annular sensing area; and an adjusting unit for adjusting the display modes of the second graphical interface according to the track of move operation.

(45) The electronic apparatus according to (44), wherein the adjusting unit is specifically for: magnifying the second graphical interface in a first preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track increases gradually.

(46) The electronic apparatus according to (44), wherein the adjusting unit is specifically for: reducing the second graphical interface in a second preset proportion according to the first sub-operational track and the second sub-operational track if it determines that the track of move operation includes the first sub-operational track and the second sub-operational track; wherein, if the first sub-operational track and the second sub-operational track are opposite in direction, the distance between the first sub-operational track and the second sub-operational track decreases gradually.

(47) The electronic apparatus according to (44), wherein the adjusting unit is specifically for: controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

(48) The electronic apparatus according to (47), wherein the adjusting unit being specifically for controlling the second graphical interface to rotate according to the first sub-operational track and the second sub-operational track is specifically: deciding whether a first operational direction corresponding to the first sub-operational track is consistent with a second operational direction corresponding to the second sub-operational track; and determining the first operational direction as rotation direction of the second graphical interface when the first operational direction is consistent with the second operational direction and controlling the second graphical interface to rotate according to the rotation direction.

(49) The electronic apparatus according to (48), wherein the adjusting module being specifically for determining the first operational direction as rotation direction of the second graphical interface when the first operational direction is consistent with the second operational direction and controlling the second graphical interface to rotate according to the rotation direction is specifically: determining the first operational direction as the rotation direction of the second graphical interface when the first operational direction is consistent with the second operational direction; determining a first angle formed by a first start point and a first end point of the first sub-operational track with the center of circle and determining a second angle formed by a second start point and a second end point of second first sub-operational track with the center of circle according to the track of move operation; determining an angle of rotation of the second graphical interface according to the first angle and the second angle; and controlling the second graphical interface to rotate according to the angle of rotation and the rotation direction.

Further, the above (14) to (31) are described by taking the technical solution according to a second embodiment being applied in the technical solution according to the first embodiment as example. Those skilled in the art can understand the technical solution according to the first embodiment may also be applied in the technical solution according to a second embodiment. In this case, the electronic apparatus according to the embodiments can be configured as follows:

(50) The electronic apparatus according to any one of (41) to (49), wherein the response unit is specifically for executing an operation of a first type as a first processing unit; and the control unit is specifically for executing an operation of a second type as a second processing unit, here, average power consumption of the second processing unit being less than average power consumption of the first processing unit;

The electronic apparatus further includes: a sharing unit connected to the response unit and the control unit and for operating cooperatively with either or both of the response unit and the control unit selectively according to predetermined condition.

(51) The electronic apparatus according to (50), wherein the frame structure body includes at least the first processing unit and the second processing unit; wherein, the fixing structure is connected to the frame main body, and the fixing unit includes at least a fixing status in which the fixing unit is able to be as an annular space or at least a part of an approximate annular space satisfying a first predetermined condition, here, the annular space or the approximate annular space is able to surround at periphery of a columnar body satisfying a second predetermined condition.

(52) The electronic apparatus according to (50), wherein the electronic apparatus includes the first processing subsystem including at least the sharing unit and the first processing unit and the second processing subsystem including at least the sharing unit and the second processing unit, average power consumption of the second processing subsystem is less than the average power consumption of the first processing subsystem.

(53) The electronic apparatus according to (52), wherein the sharing unit includes a display unit connected to the first processing unit and the second processing unit so as to display content output from the first processing unit or the second processing unit selectively according to control of the first processing unit and/or the second processing unit.

(54) The electronic apparatus according to (52), wherein, the first processing subsystem further include a first display connected to the first processing unit and for displaying content outputted from the first processing unit according to the control of the first processing unit, and the second processing subsystem may further include a second display connected to the second processing unit and for displaying content outputted from the second processing unit according to the control of the second processing unit, and average power consumption of the first display is larger than the average power consumption of the second display.

(55) The electronic apparatus according to (52), wherein the second display is further connected to the first processing unit, so that the second display displays content outputted from the first processing unit according to the control of the first processing unit; or the second processing unit is further connected to the first processing unit, so that the second processing unit receives content output from the first processing unit and control the second display to display the content received from the first processing unit when processing of the first processing unit is completed.

(56) The electronic apparatus according to (54), wherein the first display and the second display are provided overlapped in radial direction of the annular space, and when the first display or the second display provided at inner side of the radial direction of the annular space displays, it is controlled so that light transmittance of the second display or the first display provided at outer side of the radial direction of the annular space is larger than a predetermined threshold.

(57) The electronic apparatus according to (52) wherein the sharing unit further includes a power supple unit for providing electric power to the respective units of the electronic apparatus and configured to provide the electric power only to the second processing subsystem when a first predetermined condition is satisfied.

(58) The electronic apparatus according to (57), wherein the power supple unit is provided in the fixing unit.

(59) The electronic apparatus according to (52), wherein the sharing unit includes a communication unit connected to the first processing unit and the second processing unit and for connecting to network according to control of the first processing unit or the second processing unit according to a predetermined condition.

(60) The electronic apparatus according to (52), wherein the first processing subsystem includes the first communication unit and the second processing subsystem includes the second communication unit, the first communication unit is connected to the first processing unit and connected to the network according to the control of the first processing unit, the second communication unit is connected to the second processing unit and is connected to the network according to the control of the second processing unit, communication distance of the first communication unit is larger than or equal to a predetermined threshold, and communication distance of the second communication unit is less than a predetermined threshold, here, power consumption of the first communication unit is larger than that of the second communication unit;

The first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

(61) The electronic apparatus according to (52), wherein the first processing subsystem includes the first communication unit and the second communication unit which are connected to the first processing unit and connected to the network according to the control of the first processing unit, the communication distance of the first communication unit is larger than or equal to a predetermined threshold, and the communication distance of the second communication unit is less than the predetermined threshold, here, the power consumption of the first communication unit is larger than that of the second communication unit;

The first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

Each embodiment is described detailed above. However, those skilled in the art should understand, these embodiments can be made various modifications, combinations or sub-combinations without departing from the principle and spirit, and such modification should fall into the range.

Those skilled in the art should understand that, the embodiment can be provided as method, system or computer program product. Therefore, the disclosure can adopt forms of full hardware embodiment, full software embodiment, or embodiment combining software and hardware aspects. Further, any combination of one or more computer readable medium(s) may be utilized by the disclosure. The computer readable medium may be a computer readable signal medium or a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wired line, optical fiber cable, RF, etc., or any suitable combination of the foregoing.

Computer program code for carrying out operations for aspects may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In case of relating to a remote computer, the remote computer may be connected to the user's computer through any type of network, including a local area network (LAN) or a wide area network (WAN), or the connection may be made to an external computer (for example, through the Internet using an Internet Service Provider).

The disclosure is described by referring to flow chart and/or block diagram of method, apparatus (system) and computer program product according to the embodiments. It should understand that each flow and/or block in the flow chart and/or block diagram and the combination of the flow and/or block in the flow chart and/or block diagram can be implemented by computer program instruction. These computer program instruction can be provided to processors of a general purpose computer, a dedicated computer, an embedded processor or other programmable data processing apparatus to generate a machine, so that a device for implementing functions specified in one or more flow of the flow chart and/or one or more block of the block diagram is generated by the instruction executed by the processor of the computer or other programmable.

These computer program instruction can also be stored computer readable storage which is able to direct the computer or other programmable data processing apparatus to operate in specific manners, so that the instruction stored in the computer readable storage generates manufactured article including commander equipment, the commander equipment implements functions specified by one or more flow in the flow chart and/or one or more block in the block diagram.

These computer program instruction can be loaded to computer or other programmable data processing apparatus, so that a series of operation steps are executed on the computer or other programmable apparatus to generate computer implemented process, so that the instruction executed on the computer or other programmable apparatus provide steps for implementing functions specified in one or more flow of the flow chart and/or one or more block of the block diagram.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In one aspect, an application may be deployed for performing one or more aspects. As one example, the deploying of an application comprises providing computer infrastructure operable to perform one or more aspects.

As a further aspect, a computing infrastructure may be deployed comprising integrating computer readable code into a computing system, in which the code in combination with the computing system is capable of performing one or more aspects.

As yet a further aspect, a process for integrating computing infrastructure comprising integrating computer readable code into a computer system may be provided. The computer system comprises a computer readable medium, in which the computer medium comprises one or more aspects. The code in combination with the computer system is capable of performing one or more aspects.

Further, it needs to note that, in the specification, terms of "comprise", "include" and any other variation thereof intends to cover nonexclusive inclusion so that the procedure, the method, the product or the equipment including a series of elements not only includes these elements, but also include other elements which are not listed explicitly, or also include inherent elements of these procedure, method, product or equipment. In case that there is no more limitation, the element defined by statement "including one" . . . does not exclude there is additional same element in the procedure, method, article or apparatus including the element.

The corresponding structures, materials, acts, and equivalents of all means or step plus function elements in the claims below, if any, are intended to include any structure, material, or act for performing the function in combination with other claimed elements as specifically claimed. The description has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The invention claimed is:

1. An electronic apparatus comprising:
   a first processing unit for executing an operation of a first type;
   a second processing unit for executing an operation of a second type, wherein, an average power consumption of the second processing unit is less than an average power consumption of the first processing unit;
   a sharing unit connected to the first processing unit and the second processing unit for operating cooperatively selectively with either or both of the first processing unit and the second processing unit according to a predetermined condition; and
   a fixing unit for fixing relative position relation of the electronic apparatus with a user, wherein
   the electronic apparatus includes the first processing subsystem and the second processing subsystem,
   the first processing subsystem further includes a first display connected to the first processing unit for displaying content outputted from the first processing unit according to the control of the first processing unit, and the second processing subsystem further includes a second display connected to the second processing unit for displaying content outputted from the second processing unit according to the control of the second processing unit,
   the second display is further connected to the first processing unit, so that the second display displays content outputted from the first processing unit according to the control of the first processing unit; or the second processing unit is further connected to the first processing unit, so that the second processing unit receives content output from the first processing unit and control the second display to display the content received from the first processing unit when processing of the first processing unit is completed, wherein the second processing unit is configured to control the electronic apparatus to display a second graphical interface including P second identification objects for identifying application entries which are able to invoke applications corresponding to the P second identification objects in response to the first manipulation instruction, wherein, P is a positive integer.

2. The electronic apparatus according to claim 1, further comprising:

a body unit including at least the first processing unit and the second processing unit;

wherein, the fixing unit is connected to the body unit and the fixing unit includes at least a fixing status in which the fixing unit is able to be at least a part of an annular space or at least a part of an approximate annular space satisfying a first predetermined condition and the annular space or the approximate annular space is able to surround at a periphery of a columnar body satisfying a second predetermined condition.

3. The electronic apparatus according to claim 1, wherein the first processing subsystem includes at least the sharing unit and the first processing unit, and the second processing subsystem includes at least the sharing unit and the second processing unit, and an average power consumption of the second processing subsystem is less than an average power consumption of the first processing subsystem.

4. The electronic apparatus according to claim 3, wherein the first processing subsystem includes the first communication unit and the second processing subsystem includes the second communication unit, the first communication unit is connected to the first processing unit and connected to the network according to the control of the first processing unit, the second communication unit is connected to the second processing unit and is connected to the network according to the control of the second processing unit, wherein a communication distance of the first communication unit is larger than or equal to a predetermined threshold, and a communication distance of the second communication unit is less than a predetermined threshold and power consumption of the first communication unit is larger than that of the second communication unit;

the first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

5. The electronic apparatus according to claim 3, wherein the first processing subsystem includes the first communication unit and the second communication unit which are connected to the first processing unit and connected to the network according to the control of the first processing unit, the communication distance of the first communication unit is larger than or equal to a predetermined threshold the communication distance of the second communication unit is less than the predetermined threshold, wherein, the power consumption of the first communication unit is larger than that of the second communication unit;

the first communication unit stops operating according to the control of the first processing unit when the second communication unit is able to be connected to the network; and the second communication unit stops operating according to the control of the second processing unit and the first communication unit is connected to the network according to the control of the first processing unit when the second communication unit is not able to be connected to the network.

6. The electronic apparatus according to claim 1, wherein the first display and the second display are provided overlapped in radial direction of the annular space, and when the first display or the second display provided at inner side of the radial direction of the annular space displays, it is controlled so that light transmittance of the second display or the first display provided at an outer side of the radial direction of the annular space is larger than a predetermined threshold.

7. The electronic apparatus according to claim 1, further comprising:

a frame structure body including the fixing unit which is able to fix the electronic apparatus on a first operation body of a user;

a display unit fixed on the frame structure body and including a display screen;

an input unit fixed by the frame structure body and of which a sensing section is able to be positioned at any position on the frame structure body other than the display screen; and a first acquiring unit for obtaining a first manipulation instruction;

wherein, the first processing unit and the second processing unit are connected to the input unit and are fixed through the frame structure body to control the electronic apparatus according to a parameter obtained by the sensing section of the input unit;

the first processing unit is configured to control the electronic apparatus to display a first graphical interface including M first identification objects which is able to feedback working parameter of N functional modules of the electronic apparatus corresponding to the M first identification objects when the electronic apparatus is fixed on the first operation body by the fixing unit and, M and N are positive integers; and wherein, when a trigger operation with respect to an application entry corresponding to the i-th second identification object in the P second identification objects is obtained, an application corresponding to the i-th second identification object is invoked, wherein, i is a positive integer that is not larger than P.

8. The electronic apparatus according to claim 7, wherein the electronic apparatus further includes a second acquiring unit for obtaining a trigger operation with respect to an application entry corresponding to the i-th second identification object in the P second identification objects and invoking an application corresponding to the i-th second identification object.

9. The electronic apparatus according to claim 8, wherein the display screen is a circular screen, and the frame structure body includes a frame main body having a shape matched with the circular screen and for fixing the circular screen, the second graphical interface is an annular interface, a first sensing sub-section in the sensing section is provided at a locked structure of the fixing structure, and the first sensing sub-section is a circular sensing section, when the electronic apparatus is fixed on the first operation body by fixing structure, the circular screen is positioned at a first surface of the first operation body, the circular sensing section is positioned at a second surface of the first operation body, the first surface is opposite to the second surface and the circular screen is opposite to the circular sensing section; the electronic apparatus further includes:
   a third acquiring unit for obtaining a track of move operation generated by a move operation carried out on the circular sensing section by the second operation body through the circular sensing section;
   a first determining unit for determining a first position corresponding to the move operation on the circular sensing section according to the track of move operation;
   a second determining unit for determining the second identification object corresponding to the first position according to correspondence relationship between position on the circular sensing section and the second identification object; and
   an output unit for controlling to output prompt information at identification region in the second graphical interface where the determined second identification object is.

10. The electronic apparatus according to claim 7, wherein
   the display screen is a circular screen, the frame structure body includes a frame main body having a shape matched with the circular screen and for fixing the circular screen, the second graphical interface is an annular interface, a sensing section of the input unit is provided on the part of the frame main body, and a second sub-sensing section included in sensing section is at a periphery region adjacent to the display screen and the second sub sensing section is an annular sensing area and shares one center of circle with the display screen;
   the electronic apparatus further includes:
   a fourth acquiring unit for obtaining a track of move operation generated by a move operation carried out by the second operation body in the annular sensing area through the annular sensing area; and
   an adjusting unit for adjusting display modes of the second graphical interface according to the track of move operation.

11. The electronic apparatus according to claim 10, wherein the adjusting unit comprises:
   magnifying the second graphical interface in a first preset proportion according to a first sub-operational track and a second sub-operational track if it determines that the track of move operation includes the first sub-operational track and the second sub-operational track;
   wherein if the first sub-operational track and the second sub-operational track are opposite in direction, a distance between the first sub-operational track and the second sub-operational track increases gradually.

12. The electronic apparatus according to claim 10, wherein the adjusting unit comprises:
   reducing the second graphical interface in a second preset proportion according to a first sub-operational track and a second sub-operational track if it determines that the track of move operation includes the first sub-operational track and the second sub-operational track;
   wherein if the first sub-operational track and the second sub-operational track are opposite in direction, the distance between the first sub-operational track and the second sub-operational track decreases gradually.

13. The electronic apparatus according to claim 10, wherein the adjusting unit comprises controlling the second graphical interface to rotate according to the first sub-operational track and the second sub-operational track if it determines that the track of move operation includes the first sub-operational track and the second sub-operational track and the first sub-operational track and the second sub-operational track are not positioned at a same line.

14. The electronic apparatus according to claim 13, wherein the adjusting unit for controlling the second graphical interface to rotate according to the first sub-operational track and the second sub-operational track comprises:
   deciding whether a first operational direction corresponding to the first sub-operational track is consistent with a second operational direction corresponding to the second sub-operational track; and
   determining the first operational direction as rotation direction of the second graphical interface when the first operational direction is consistent with the second operational direction and controlling the second graphical interface to rotate according to the rotation direction.

15. The electronic apparatus according to claim 14, wherein the adjusting module for determining the first operational direction as rotation direction of the second graphical interface when the first operational direction is consistent with the second operational direction and controlling the second graphical interface to rotate according to the rotation direction comprises:
   determining the first operational direction as the rotation direction of the second graphical interface when the first operational direction is consistent with the second operational direction;
   determining a first angle formed by a first start point and a first end point of the first sub-operational track with the center of circle and determining a second angle formed by a second start point and a second end point of second first sub-operational track with the center of circle according to the track of move operation;
   determining an angle of rotation of the second graphical interface according to the first angle and the second angle; and
   controlling the second graphical interface to rotate according to the angle of rotation and the rotation direction.

16. The electronic apparatus according to claim 1, wherein an average power consumption of the first display is larger than an average power consumption of the second display.

17. An information processing method applied in an electronic apparatus including a fixing unit for fixing relative position relation of the electronic apparatus with a user, the information processing method comprises:
   executing an operation of a first type by a first processing unit of the electronic apparatus;
   executing an operation of a second type by a second processing unit of the electronic apparatus, where average power consumption of the second processing unit is less than average power consumption of the first processing unit; and
   operating cooperatively with either or both of the first processing unit and the second processing unit selectively by a sharing unit of the electronic apparatus according to predetermined conditions, wherein, the sharing unit is connected to the first processing unit and the second processing unit, wherein the electronic apparatus includes the first processing subsystem and the second processing subsystem, the first processing subsystem further includes a first display connected to the first processing unit, and the second processing subsystem further includes a second display connected to the second processing unit, executing an operation of displaying content outputted from the first processing unit according to the control of the first processing unit by the first display;

executing an operation of displaying content outputted from the second processing unit according to the control of the second processing unit by the second display; wherein the second display is further connected to the first processing unit, so that executing an operation of displaying content outputted from the first processing unit according to the control of the first processing unit by the second display; or the second processing unit is further connected to the first processing unit, so that executing an operation of receiving content output from the first processing unit and controlling the second display to display the content received from the first processing unit when processing of the first processing unit is completed by the second processing unit, wherein, controlling the electronic apparatus to display a second graphical interface including P second identification objects for identifying application entries which are able to invoke applications corresponding to the P second identification objects by the first processing unit in response to the first processing unit, wherein, P is a positive integer.

18. The information processing method according to claim 17, wherein the electronic apparatus further comprises:

a frame structure body including a fixing structure which is able to fix the electronic apparatus on a first operation body;

a display unit fixed on the frame structure body and including a display screen; and an input unit fixed by the frame structure body and of which a sensing section is able to be positioned at any position on the frame structure body other than the display screen;

the first processing unit and the second processing unit are connected to the input unit and are fixed through the frame structure body and control the electronic apparatus according to parameter obtained by the sensing section of the input unit;

the information processing method further includes:

obtaining a first manipulation instruction;

executing the operation of the second type by the second processing unit of the electronic apparatus comprises:

controlling the electronic apparatus to display a first graphical interface including M first identification objects which are able to feedback working parameter of N functional modules corresponding to the M first identification objects of the electronic apparatus in real time by the second processing unit when the electronic apparatus is fixed on the first operation body by the fixing structure, wherein, M and N being positive integers; and executing the operation of the first type by the first processing unit of the electronic apparatus comprises:

wherein, when a trigger operation with respect to an application entry corresponding to the i-th second identification object in the P second identification objects is obtained, an application corresponding to the i-th second identification object is invoked, wherein, i is a positive integer that is not larger than P.

19. The information processing method according to claim 18, wherein the display screen is a circular screen, the frame structure body includes a frame main body having a shape matched with the circular screen and for fixing the circular screen, the second graphical interface is an annular interface, a sensing section of the input unit is provided on the part of the frame main body, and a second sub-sensing section included in sensing section is at a periphery region adjacent to the display screen and the second sub sensing section is an annular sensing area and shares one center of circle with the display screen;

after controlling the electronic apparatus to display the second graphical interface in response to the first manipulation instruction, the method further includes:

obtaining a track of move operation generated by a move operation carried out by the second operation body in the annular sensing area through the annular sensing area; and adjusting display modes of the second graphical interface according to the track of move operation.

* * * * *